(12) United States Patent
Malofsky et al.

(10) Patent No.: US 10,604,601 B2
(45) Date of Patent: Mar. 31, 2020

(54) MULTIFUNCTIONAL MONOMERS, METHODS FOR MAKING MULTIFUNCTIONAL MONOMERS, POLYMERIZABLE COMPOSITIONS AND PRODUCTS FORMED THEREFROM

(71) Applicant: Sirrus, Inc., Loveland, OH (US)

(72) Inventors: Bernard M. Malofsky, Bloomfield, CT (US); Adam G. Malofsky, Loveland, OH (US); Tanmoy Dey, Willington, CT (US); Matthew M. Ellison, Mason, OH (US); Larry Hines, Odessa, TX (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/978,974

(22) Filed: May 14, 2018

(65) Prior Publication Data
US 2018/0327525 A1 Nov. 15, 2018

Related U.S. Application Data

(63) Continuation of application No. 15/289,300, filed on Oct. 10, 2016, now Pat. No. 9,969,822, which is a continuation of application No. 14/352,356, filed as application No. PCT/US2012/060830 on Oct. 18, 2012, now Pat. No. 9,512,058.

(60) Provisional application No. 61/549,104, filed on Oct. 19, 2011, provisional application No. 61/549,092, filed on Oct. 19, 2011, provisional application No. 61/549,152, filed on Oct. 19, 2011.

(51) Int. Cl.
| | |
|---|---|
| C07C 45/75 | (2006.01) |
| C07C 49/794 | (2006.01) |
| C07C 49/796 | (2006.01) |
| C07C 49/798 | (2006.01) |
| C07C 49/80 | (2006.01) |
| C07C 67/03 | (2006.01) |
| C07C 67/30 | (2006.01) |
| C07C 69/604 | (2006.01) |
| C08F 20/28 | (2006.01) |
| C09J 133/06 | (2006.01) |
| C08F 222/10 | (2006.01) |
| C08F 20/14 | (2006.01) |
| C09D 4/00 | (2006.01) |

(Continued)

(52) U.S. Cl.
CPC ............. *C08F 20/28* (2013.01); *C07C 45/75* (2013.01); *C07C 49/794* (2013.01); *C07C 49/796* (2013.01); *C07C 49/798* (2013.01); *C07C 49/80* (2013.01); *C07C 67/03* (2013.01); *C07C 67/30* (2013.01); *C07C 69/604* (2013.01); *C07C 69/738* (2013.01); *C07D 307/46* (2013.01); *C07D 307/54* (2013.01); *C07D 333/22* (2013.01); *C07D 333/24* (2013.01); *C08F 20/14* (2013.01); *C08F 20/30* (2013.01); *C08F 20/38* (2013.01); *C08F 20/68* (2013.01); *C08F 22/20* (2013.01); *C08F 24/00* (2013.01); *C08F 28/06* (2013.01); *C08F 116/36* (2013.01); *C08F 128/06* (2013.01); *C08F 222/1006* (2013.01); *C08F 222/14* (2013.01); *C08K 3/013* (2018.01); *C08K 5/0008* (2013.01); *C08L 21/00* (2013.01); *C08L 33/14* (2013.01); *C08L 33/16* (2013.01); *C08L 35/02* (2013.01); *C09D 4/00* (2013.01); *C09D 129/12* (2013.01); *C09D 133/14* (2013.01); *C09D 133/16* (2013.01); *C09D 135/02* (2013.01); *C09D 141/00* (2013.01); *C09J 133/06* (2013.01); *C09J 133/14* (2013.01); *C09J 133/16* (2013.01); *C09J 135/02* (2013.01); *C07C 2601/14* (2017.05); *Y02P 20/127* (2015.11)

(58) Field of Classification Search
CPC ....... C08F 20/28; C07C 67/30; C07C 69/738; C07C 67/03; C07C 49/794
See application file for complete search history.

(56) References Cited

U.S. PATENT DOCUMENTS

| | | | |
|---|---|---|---|
| 2,230,033 A | | 1/1941 | Hackett |
| 2,277,479 A | * | 3/1942 | D Alelio ............ C08G 16/0225 528/224 |

(Continued)

FOREIGN PATENT DOCUMENTS

| | | |
|---|---|---|
| DE | 102017204525 A1 | 9/2017 |
| FR | 2788516 A1 | 7/2000 |

(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX . (Year: 2005).*

(Continued)

*Primary Examiner* — Paul A Zucker
(74) *Attorney, Agent, or Firm* — Young Basile Hanlon & MacFarlane, P.C.

(57) ABSTRACT

The present invention provides multifunctional monomers, including, but not limited to include multifunctional methylene malonate and methylene beta-ketoester monomers; methods for producing the same; and compositions and products formed therefrom. The multifunctional monomers of the invention may be produced by transesterification or by direct synthesis from monofunctional methylene malonate monomers or methylene beta-ketoester monomers. The present invention further compositions and products formed from methylene beta-ketoester monomers of the invention, including monomer-based products (e.g., inks, adhesives, coatings, sealants or reactive molding) and polymer-based products (e.g., fibers, films, sheets, medical polymers, composite polymers and surfactants).

20 Claims, No Drawings

(51) Int. Cl.

| | |
|---|---|
| *C08K 3/013* | (2018.01) |
| *C07D 307/46* | (2006.01) |
| *C07D 333/22* | (2006.01) |
| *C08F 116/36* | (2006.01) |
| *C08F 128/06* | (2006.01) |
| *C09D 129/12* | (2006.01) |
| *C09D 141/00* | (2006.01) |
| *C07C 69/738* | (2006.01) |
| *C07D 307/54* | (2006.01) |
| *C07D 333/24* | (2006.01) |
| *C08F 20/68* | (2006.01) |
| *C08F 24/00* | (2006.01) |
| *C08F 28/06* | (2006.01) |
| *C08F 222/14* | (2006.01) |
| *C08F 20/30* | (2006.01) |
| *C08F 20/38* | (2006.01) |
| *C08F 22/20* | (2006.01) |
| *C08K 5/00* | (2006.01) |
| *C08L 21/00* | (2006.01) |
| *C08L 33/14* | (2006.01) |
| *C08L 33/16* | (2006.01) |
| *C08L 35/02* | (2006.01) |
| *C09D 133/14* | (2006.01) |
| *C09D 133/16* | (2006.01) |
| *C09D 135/02* | (2006.01) |
| *C09J 133/14* | (2006.01) |
| *C09J 133/16* | (2006.01) |
| *C09J 135/02* | (2006.01) |

(56) References Cited

U.S. PATENT DOCUMENTS

| | | |
|---|---|---|
| 2,313,501 A | 3/1943 | Bachman |
| 2,330,033 A | 9/1943 | D'Aiello |
| 3,042,710 A | 7/1962 | Dickstein et al. |
| 3,197,318 A | 7/1965 | Halpern et al. |
| 3,221,745 A | 12/1965 | Coover |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender et al. |
| 3,936,486 A | 2/1976 | Egger et al. |
| 3,975,422 A | 8/1976 | Buck |
| 3,978,422 A | 8/1976 | Rheinfelder |
| 3,995,489 A | 12/1976 | Smith et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,154,914 A | 5/1979 | Kuraya |
| 4,160,864 A | 7/1979 | Ponticello et al. |
| 4,198,334 A | 4/1980 | Rasberger |
| 4,237,297 A | 12/1980 | Rody et al. |
| 4,256,908 A | 3/1981 | Nishimura et al. |
| 4,329,479 A | 5/1982 | Yabutani et al. |
| 4,399,300 A | 8/1983 | Prange et al. |
| 4,443,624 A | 4/1984 | Prange et al. |
| 4,444,928 A | 4/1984 | Karrer |
| 4,504,658 A | 3/1985 | Narisada et al. |
| 4,517,105 A | 5/1985 | Laemmle et al. |
| 4,539,423 A | 9/1985 | Itatani et al. |
| 4,556,649 A | 12/1985 | Salzburg et al. |
| 4,578,503 A | 3/1986 | Ishikawa et al. |
| 4,613,658 A | 9/1986 | Mathias et al. |
| 4,698,333 A | 10/1987 | Fauss et al. |
| 4,727,701 A | 3/1988 | Figari |
| 4,728,701 A | 3/1988 | Jarvis et al. |
| 4,736,056 A | 4/1988 | Smith et al. |
| 4,769,464 A | 9/1988 | Sajtos |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,259,835 A | 11/1993 | Clark et al. |
| 5,292,937 A | 3/1994 | Manning et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,575,997 A | 11/1996 | Leung et al. |
| 5,582,834 A | 12/1996 | Leung et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,069,261 A | 5/2000 | Hoffmann et al. |
| 6,106,807 A | 8/2000 | Albayrak et al. |
| 6,143,352 A | 11/2000 | Clark et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,300,045 B2 | 10/2001 | Lobo et al. |
| 6,395,737 B1 | 5/2002 | Defossa et al. |
| 6,395,931 B1 | 5/2002 | Carvalho et al. |
| 6,420,468 B2 | 7/2002 | Bru-Magniez et al. |
| 6,440,461 B1 | 8/2002 | Bru-Magniez et al. |
| 6,506,862 B2 | 1/2003 | Cabioch et al. |
| 6,512,023 B1 | 1/2003 | Malofsky et al. |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,750,298 B1 | 6/2004 | Bru-Magniez et al. |
| 6,794,365 B2 | 9/2004 | Al-Obeidi et al. |
| 6,846,783 B2 | 1/2005 | Bartley et al. |
| 7,056,540 B2 | 6/2006 | Yadav et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,465,773 B2 | 12/2008 | Kodemura et al. |
| 7,553,989 B2 | 6/2009 | Sawabe et al. |
| 7,576,234 B2 | 8/2009 | Chorghade et al. |
| 7,626,477 B2 | 12/2009 | Huang et al. |
| 7,629,416 B2 | 12/2009 | Li et al. |
| 7,659,423 B1 | 2/2010 | McArdle |
| 7,663,000 B2 | 2/2010 | Dekkers et al. |
| 7,900,558 B2 | 3/2011 | Yokoi |
| 8,110,641 B2 | 2/2012 | Lee et al. |
| 8,138,270 B2 | 3/2012 | Sasagawa et al. |
| 8,168,213 B2 | 5/2012 | Kangas et al. |
| 8,247,508 B2 | 8/2012 | Takashima et al. |
| 8,332,437 B2 | 12/2012 | Ballard et al. |
| 8,344,156 B2 | 1/2013 | Umetani et al. |
| 8,425,790 B2 | 4/2013 | Sato et al. |

(56) References Cited

U.S. PATENT DOCUMENTS

| | | | |
|---|---|---|---|
| 8,554,938 B2 | 10/2013 | Mittal | |
| 8,609,885 B2 | 12/2013 | Malofsky et al. | |
| 8,722,831 B2 | 5/2014 | Arai et al. | |
| 8,884,051 B2 | 11/2014 | Malofsky et al. | |
| 8,975,435 B2 | 3/2015 | Malofsky et al. | |
| 8,992,512 B2 | 3/2015 | Richard et al. | |
| 8,993,795 B2 | 3/2015 | Malofsky et al. | |
| 9,108,914 B1 | 8/2015 | Malofsky et al. | |
| 9,181,365 B2 | 11/2015 | Malofsky et al. | |
| 9,217,098 B1 | 12/2015 | Stevenson et al. | |
| 9,220,811 B2 | 12/2015 | Overstreet et al. | |
| 9,221,739 B2 | 12/2015 | Malofsky et al. | |
| 9,234,107 B2 | 1/2016 | Malofsky et al. | |
| 9,334,430 B1 | 5/2016 | Stevenson et al. | |
| 9,505,943 B2 | 11/2016 | Overbeek et al. | |
| 9,512,058 B2* | 12/2016 | Malofsky | C09J 133/06 |
| 9,523,008 B2 | 12/2016 | Malofsky et al. | |
| 9,752,059 B2 | 9/2017 | Malofsky et al. | |
| 9,969,822 B2* | 5/2018 | Malofsky | C09J 133/06 |
| 10,047,192 B2 | 8/2018 | Ellison et al. | |
| 2004/0076601 A1 | 4/2004 | Bru-Magniez et al. | |
| 2007/0049655 A1 | 3/2007 | Yoshimune et al. | |
| 2007/0092483 A1 | 4/2007 | Pollock | |
| 2008/0160305 A1 | 7/2008 | Warren et al. | |
| 2011/0059104 A1 | 3/2011 | Escandon et al. | |
| 2011/0164322 A1 | 7/2011 | Morozumi et al. | |
| 2014/0248485 A1 | 9/2014 | Malofsky et al. | |
| 2015/0056879 A1 | 2/2015 | Malofsky et al. | |
| 2015/0303122 A1 | 10/2015 | Malofsky et al. | |
| 2018/0010014 A1 | 1/2018 | Sweet et al. | |

FOREIGN PATENT DOCUMENTS

| | | | |
|---|---|---|---|
| GB | 432628 A | | 7/1935 |
| GB | 965676 A | | 8/1964 |
| GB | 975733 A | | 11/1964 |
| JP | 08231564 H | | 9/1996 |
| JP | 09258448 A | | 10/1997 |
| JP | 2000199936 A | * | 7/2000 |
| JP | 2003201397 A | | 7/2003 |
| WO | 1999/046619 A1 | | 9/1999 |
| WO | 2011/161045 A1 | | 12/2011 |
| WO | 2012/054633 A2 | | 4/2012 |
| WO | 2013/149165 A1 | | 10/2013 |
| WO | 2013/149168 A1 | | 10/2013 |
| WO | 2013/149173 A1 | | 10/2013 |
| WO | 2017/184986 A1 | | 10/2017 |
| WO | 2018/022780 A1 | | 2/2018 |
| WO | 2018/022785 A1 | | 2/2018 |
| WO | 2018/022788 A1 | | 2/2018 |
| WO | 2018/022792 A1 | | 2/2018 |
| WO | 2018/022794 A1 | | 2/2018 |
| WO | 2018/022804 A1 | | 2/2018 |
| WO | 2018/022810 A1 | | 2/2018 |
| WO | 2018/053454 A1 | | 3/2018 |
| WO | 2018/053503 A1 | | 3/2018 |
| WO | 2018/086860 A1 | | 5/2018 |

OTHER PUBLICATIONS

McCoy, M. "A New Way to Stick" Chemical & Engineering News, vol. 92, Issue 26, Jun. 30, 2014, pp. 17-18, paragraph [2].

Bachman et al., "Diethyl Methylenemalonate" Contirbution from the Research Laboratories of the Eastman Kodak Dompany, May 17, 1939, pp. 493-501.

"Knoevenagel reaction on a molecular sieve", Li Qifang et al., Chinese Science Bulletin, 1988, vol. 12, pp. 914-917.

"Knoevenagel Condensation Over Acidic Zeolite", Zuo Bojun et al., Chinese Journal of Catalysis, Nov. 2002, vol. 23 (6), pp. 555-558.

"Comparison of the catalytic activity of MOFs and zeolites in Knoevenagel condensation", Maksym Opanasenko, et al., Catalysis Science & Technology, 2013, vol. 3 p. 500-507.

Corey et al. "Total Synthesis of Gibberellic Acid. A Simple Synthesiss of a Key Intermediate", J. Am. Chem. Soc. 1982, 104, 6129-6130.

Krishna et al. "Stereodefined Access to 3-Deoxy Sugars Through a Tandem Baylis-Hillman and Lewis Acid Catalyzed Sequence", European Journal of Organic Chemistry, 2010, 813-817.

European Patent Office Communication Pursuant to Rule 164(1) EPC for Application No. 12842316.7 dated May 19, 2016

Office Action from the Japanese Patent Office for Application No. 2014-537248, dated Jun. 7, 2016.

Extended European Search Report for Application No. PCT/US2012060830 dated Sep. 5, 2016.

International Search Report and Written Opinion for PCT Application No. PCT/US2012/60830 dated Feb. 1, 2013 (U.S. Appl. No. 14/352,356).

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.

McNab, Kirk-Othmer Encyclopedia of chemical Technology, Pyrolysis, Flash Vacuum, 2009, John Wiley & Sons, Inc., pp. 1-26.

Block, "Diethyl bis (hydroxymethyl) malonate"Organic Syntheses, 1973, Coll. vol. 5, p. 381 [vol. 40, p. 27 (1960); Retrieved on Apr. 4, 2014 from internet: Hyperlink "http://www.Orgsyn.org/content/pdfs/procedures/cv5p0381.pdf" http://www.Orgsyn.org/content/pdfs/procedures/cv5p0381.pdf ] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl glioiosiphne A by Way of Palladium-Catalyzed Domino Cyclization," T. Org <http://T.Org>. Chem., (2007), vol. 72, pp. 3667-3671.

H. Jung et al,: "New and General Methods for the Synthesis of Arylmethylene Bis(3-Hydroxy-2-Cyclohexene-1-Ones) and Xanthenediones by EDDA and In(OTf)3-Catalyzed One-Pot Domino Knoevenagel/Michael or Koevenagel/Michael/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,- (1998), vol. 39, No. I, pp. 173-181.

C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a.

P, Ballesteros et al.: "Dl-tert-Butyl Methylenemalonate [Propanedioic Acid, Methylene-, bis(1,1-dimethylethyl)ester]," Organic Syntheses. Coll. (1990), vol. 7, p. 142 ; (1986) vol. 64, p. 63.

(56) References Cited

OTHER PUBLICATIONS

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327- 2330.

G. Lai et al.: "Ionic Liquid Functionalized Silica Gel: Novel Catalyst and Fixed Solvent," Tetrahedron Letters (2006), vol. 47, pp. 6951-6953.

J.R. Harjani et al.: "Lewis Acidic Ionic Liquids for the Synthesis of Electrophilic Alkenes ; via the Knoevenagel Condensation," Tetrahedron Letters, (2002), vol. 43, pp. 1127-1130.

P. Ballesteros et al.: "Synthesis of Dl-tent-Butyl Methylenemalonate, a Sterically Hindered 1,1-Dicarbonyl Alkene," J. Org <http://J.Org>. Chem, (1983), vol. 48, pp. 3603-3605.

\* cited by examiner

MULTIFUNCTIONAL MONOMERS, METHODS FOR MAKING MULTIFUNCTIONAL MONOMERS, POLYMERIZABLE COMPOSITIONS AND PRODUCTS FORMED THEREFROM

CROSS REFERENCE TO RELATED APPLICATIONS

This application is a continuation of co-pending application Ser. No. 15/289,300, U.S. Pat. No. 9,969,822, filed Oct. 10, 2016, with is a continuation of co-pending application Ser. No. 14/352,356, U.S. Pat. No. 9,512,058, filed Apr. 17, 2014 which is a national application pursuant to 35 USC 371 of application PCT/US2012/60830 filed Oct. 18, 2012; this application and PCT/US2012/60830 claim priority to Provisional Patent Applications 61/549,104, filed Oct. 19, 2011; 61/549,092, filed Oct. 19, 2011; and 61/549,152, filed Oct. 19, 2011; and the contents of these applications are in their entirety hereby incorporated herein by reference.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to multifunctional monomers, to methods of producing or synthesizing such monomers, and to the use and application of such monomers as commercial products and compositions, including, for example, monomer-based products (e.g., inks, adhesives, coatings, sealants or reactive molding) and polymer-based products (e.g., fibers, films, sheets, medical polymers, composite polymers and surfactants).

Specific embodiments are directed to multifunctional methylene malonate and methylene beta-ketoester monomers but the principles disclosed herein are relevant to other disubstituted vinyl compounds having electron withdrawing groups in the beta position.

2. Background

Methylene malonate monomers, methylene beta-ketoester monomers and their associated monomeric and polymeric-based products would be useful in both industrial (including household) and medical applications. Indeed, unlike many other monomers, these monomers and their products can be produced via sustainable routes as well as be designed to be environmentally benign, biologically benign and as such many of the products can be generally regarded as "green."

Methylene malonate monomers and methylene beta-ketoester monomers have the potential to form the basis of a large-scale platforms of new raw materials for the generation of a wide variety of new chemical products, including inks, adhesives, coatings, sealants, moldings, fibers, films, sheets, medical polymers, composites, surfactants and the like. While the production of monofunctional methylene malonates by various processes has been known for many years, these earlier methods suffer significant deficiencies that preclude their use in obtaining viable monomers for commercial exploitation. Such deficiencies in these older methods include unwanted polymerization of the monomers during synthesis (e.g., formation of polymers or oligomers or alternative complexes), formation of undesirable side products (e.g., ketals or other latent acid-forming species which impede rapid polymerization), and degradation of the product, insufficient and/or low yields, and ineffective and/or poorly functioning monomer product (e.g., poor adhesive characteristics or other functional characteristics), among other problems. The overall poorer yield, quality, and chemical performance of the monomer products formed by prior art methods impinges on their practical use in the production of the above commercial and industrial products. No viable solutions to solve the aforementioned problems have yet been proposed, accepted and/or recognized and certainly do not exist currently in the industry.

In the art, numerous attempts overall have been made to functionalize highly activated disubstituted vinyl monomers, particularly cyanoacrylates. Cyanoacrylate adhesives are one-part solvent-free adhesives that cure rapidly through polymerization at room temperature. These adhesives are used in a wide range of applications across various industries as a result of their fast and often strong shear strength. Unfortunately, while the cyanoacrylic anionic cure mechanism is facile, poor impact and environmental resistance has vastly limited their potential from the broad array of applications that thermosetting systems allow. For example, thermosetting systems provide the benefits of cross-linking and allow for a particular physical or chemical trait to be introduced via a multifunctional resin. While attempts have been made to produce multifunctional systems for cyanoacrylates they have not been met with any commercial success due to poor yields, poor stability and high costs. Monomeric systems in the prior art either go through a blocking agent process, the incorporation of a secondary cure or similar processes. Multifunctional cyanoacetates converted to cyanoacrylates simply cannot be cracked to monomer the same way that a monofunctional cyanoacrylate monomer is made now.

Conversely, while their cure is slower, crosslinked epoxies, polyurethanes, polyesters, silicones polyimides, polyureas and the like provide excellent properties but require heat and/or mixing and relatively long cure times that are energy intensive to polymerize. Multifunctional acrylic systems polymerize quickly, but only at high catalyst loading, and/or through the use of external energy sources or primers.

The prior art's attempts at delivering a multifunctional system have been met with no commercial success and require long cure times for ultimate strength and display poor stability due the use of an allylic functionality. The prior art also cannot deliver the wide range of properties that a functionalized resin can nor can deliver a functionality greater than 2 as described in the art.

Accordingly, it would of great utility if multifunctional 1, 2 substituted methylene malonates and methylene beta-ketoesters could be produced not only as reactive monomers but also incorporated as reactive groups along oligomeric and polymeric backbones. It would be of even further use to not only employ such monomers, oligomers and polymers as polymerizable molecules, but to also functionalize them for other purposes, such as conducting chemistry on the methylene malonates to create other functional groups, such as dyes, catalysts, chelating agents, medicals, anti-fungal agents and the like or to polymerize off of them other monomers to create not a crosslinked system but alternatively a unique copolymer system, such as a polyolefin off of certain parts of a polyester.

Also of utility would be the ability to use a process for easily producing certain base methylene malonate monomers or methylene beta-ketoester monomers and then to use a second process to convert those into more complex, difficult to produce and/or higher molecular weight methylene malonate monomers or methylene beta-ketoester monomers.

Thus, multifunctional monomers, i.e. monomers having two or more methylene double bonds, would be of interest as they could be selectively functionalized or crosslinked. No viable routes to multifunctional methylene malonate monomers have yet to be proposed, accepted and/or recognized and certainly do not exist currently in the industry.

Further, a need exists for methods for synthesizing methylene malonate monomers and methylene beta-ketoester monomers and others that are capable of being viably used in commercial and industrial applications.

SUMMARY OF THE INVENTION

The purpose and advantages of the present invention will be set forth in and shall be apparent from the description that follows. Additional advantages of the invention will be realized and attained by the methods and systems particularly pointed out in the written description and claims hereof, as well as from the appended drawings.

In one aspect, the invention provides a multifunctional monomer having the formula:

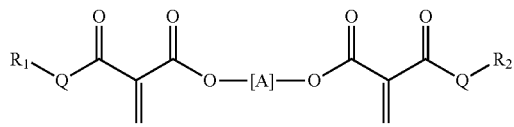

wherein:

each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

-[A]- represents —$(CR^AR^B)_n$—, —$(CR^AR^B)_n$—O(C=O)—$(CH_2)_{1-15}$—(C=O)O—$(CR^AR^B)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

each instance of $R^A$ or $R^B$ is independently H, $C_1$-$C_{15}$ alkyl, $C_2$-$C_{15}$ alkenyl, a moiety represented by the formula:

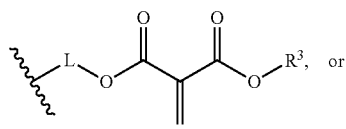

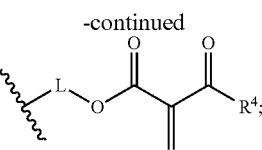

wherein:

-L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

$R^3$ is independently selected from the group defined in $R^2$ above; and $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;

—[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group each instance of n is independently an integer from 1 to 25; and each instance of Q represents —O— or a direct bond.

In another aspect, the invention provides a multifunctional monomer having the formula:

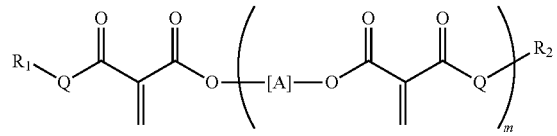

wherein:

each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

-[A]- represents —$(CR^AR^B)_n$—, —$(CR^AR^B)_n$—O(C=O)—$(CH_2)_{1-15}$—(C=O)O—$(CR^AR^B)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

each instance of $R^A$ or $R^B$ is independently H, $C_1$-$C_{15}$ alkyl, $C_2$-$C_{15}$ alkenyl, a moiety represented by the formula:

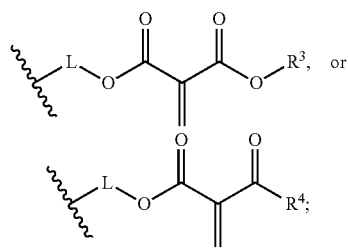

wherein:
- -L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- $R^3$ is independently selected from the group defined in $R^2$ above; and
- $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- —[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group
- n is an integer from 1 to 25;
- m is an integer from 1 to 25;
- each instance of Q represents —O— or a direct bond.

In still another aspect, the invention provides a method for making a multifunctional methylene malonate monomer. The method comprises:
(a) reacting a sufficient amount of at least one first methylene malonate monomer with a sufficient amount of a diol, a polyol or a polymeric resin having at least two hydroxyl groups in the presence of a catalyst, under suitable reaction conditions and sufficient time, to form a reaction complex; and
(b) recovering multifunctional methylene malonate monomer from the reaction complex.

In certain embodiments, the reacting step (a) is performed at room temperature and at atmospheric pressure. In other embodiments, the reacting step (a) is performed at elevated temperature and at atmospheric pressure. In still other embodiments, the reacting step (a) is performed at room temperature and under vacuum. In yet other embodiments, the reacting step (a) is performed at elevated temperature and under vacuum.

In yet another aspect, the invention provides a method of making a multifunctional beta-ketoester monomer comprising:
(a) reacting a sufficient amount of at least one first methylene beta-ketoester monomer with a sufficient amount of a diol, a polyol or a polymeric resin having at least two hydroxyl groups in the presence of a catalyst, under suitable reaction conditions and sufficient time, to form a reaction complex;
(b) recovering multifunctional methylene beta-ketoester monomer from the reaction complex.

In still another aspect, the invention provides a method of making a multifunctional methylene malonate monomer comprising:
(a) reacting a malonic acid ester or a malonic acid chloride with a diol, a polyol, or a polymeric resin comprising at least two hydroxyl groups to form a multifunctional malonic acid ester;
(b) reacting the multifunctional malonic acid ester formed in step (a) with a source of formaldehyde; optionally in the presence of an acidic or basic catalyst; and optionally in the presence of an acidic or non-acidic solvent; and optionally in the presence of an acid scavenger to form a reaction complex; and
(c) recovering multifunctional methylene malonate monomer from the reaction complex.

In certain embodiments, utilizing a malonic acid ester, the malonic acid ester has the formula:

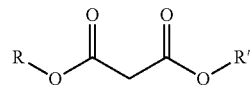

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain embodiments, the multifunctional methylene malonates and the multifunctional methylene beta-ketoester monomers formed according to the methods disclosed herein are capable of bonding glass to a substrate in less than about 90 seconds, less than about 60 seconds, less than about 30 seconds or less than about 15 seconds.

In other embodiments, the multifunctional methylene malonates and the multifunctional methylene beta-ketoester monomers formed according to the methods disclosed herein are capable of bonding polycarbonate to a substrate in less than about 90 seconds, less than about 60 seconds, less than about 45 seconds or less than about 30 seconds.

In exemplary embodiments, the multifunctional methylene malonates and the multifunctional methylene beta-ketoester monomers formed according to the methods disclosed herein are amenable to anionic polymerization.

In yet other embodiments, said composition remains stable at 25° C. and at atmospheric pressure for more than 10 days, more than 15 days, more than 20 days, more than 25 days or more than 30 days. In still yet other embodiments, said composition remains stable at 82° C. and at atmospheric pressure for more than about 2 hours, more than about 3 hours, or more than about 4 hours.

In certain embodiments, the monomers and polymers of the invention are useful in products, including, but not limited to, adhesives, coating compositions and sealants. Other exemplary products obtained from multifunctional methylene malonate monomers or methylene beta-ketoester monomers include thermal barrier coatings, textile fibers, water-treatment polymers, ink carriers, paint carrier, packaging film, moldings, medical polymer, a polymer film, a polymer fiber, and a polymer sheet.

In certain embodiments, the products are formulated to include acidic stabilizers, free radical stabilizers, sequestering agents, cure accelerators, rheology modifiers, plasticizing agents, thixotropic agents, natural rubbers, synthetic rubbers, filler agents, reinforcing agents, plasticizers, or any combination thereof.

In certain embodiments, the product is stable for at least one year.

DESCRIPTION OF THE INVENTION

Overview

The present invention provides novel multifunctional methylene malonate monomers and multifunctional beta-ketoester monomers, methods of synthesis thereof, and formulated products and polymers.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "methylene malonate" refers to a compound having the core formula —O—C(O)—C(=CH$_2$)—C(O)—O—.

As used here, the term "malonic acid ester" refers to a compound having the core formula —O—C(O)—CH$_2$—C(O)—O—.

As used herein, the term "monofunctional" refers to a malonic acid ester or a methylene malonate having only one core formula.

As used herein, the term "difunctional" refers to a malonic acid ester or a methylene malonate having two core formulas.

As used herein, the term "multifunctional" refers to refers to a malonic acid ester or a methylene malonate having more than one core formulas. Thus the term "difunctional" is encompassed within the term "multifunctional."

As used herein, the term "reaction complex" refers to the materials which result after the initial reaction step(s) for each scheme. In certain embodiments, the "reaction complex" refers to the materials of the reaction prior to the isolation of product. Such reaction complexes may comprise, without limitation, multifunctional methylene malonate monomers, oligomeric complexes, irreversible complex impurities, starting materials, or latent acid-forming impurities.

As used herein, the term "reaction vessel" refers to any container in which the reactants, solvents, catalysts or other materials may be combined for reaction. Such reaction vessels can be made of any material known to one of skill in the art such as metal, ceramic or glass.

As used herein, the term "recovering" or "obtaining" or "isolating" as in "isolating the multifunctional methylene malonate monomer," refers to the removal or collection of the monomer from the reaction complex by a method described herein, or understood by those having skill in the art. As used herein, "recovering" or "isolating" does not necessarily imply that a reaction product has been obtained in a substantially pure form.

As used herein, the term "latent acid-forming impurities" or "latent acid-forming impurity" refers to any impurity that, if present along with the recovered methylene malonate monomer, will with time be converted to an acid. The acid formed from these impurities tends to result in overstabilization of the multifunctional methylene malonate monomer, thereby reducing the overall quality and reactivity of the monomer.

As used herein, the term "ketal" refers to molecule having a ketal functionality; i.e. a or molecule containing a carbon bonded to two —OR groups, where O is oxygen and R represents any alkyl group.

As used herein the term "substantial absence" as in "substantial absence of acidic solvent" refers to a reaction mixture which comprises less than 1% by weight of the particular component as compared to the total reaction mixture. In certain embodiments, a "substantial absence" refers to less than 0.7%, less than 0.5%, less than 0.4% m less than 0.3%, less than 0.2% or less than 0.1% by weight of the of the particular component as compared to the total reaction mixture. In certain other embodiments, a "substantial absence" refers to less than 1.0%, less than 0.7%, less than 0.5%, less than 0.4% m less than 0.3%, less than 0.2% or less than 0.1% by volume of the of the particular component as compared to the total reaction mixture.

As used herein, the term "stabilized," e.g., in the context of "stabilized" molecules of the invention or compositions comprising same, refers to the tendency of the molecules of the invention (or their compositions) to substantially not polymerize with time, to substantially not harden, form a gel, thicken, or otherwise increase in viscosity with time, and/or to substantially show minimal loss in cure speed (i.e., cure speed is maintained) with time as compared to similar compositions that are not stabilized.

As used herein, the term "shelf-life," e.g., as in the context of the molecules of the invention having an improved "shelf-life," refers to the molecules of the invention which are stabilized for a given period of time, e.g., 1 month, 6 months, or even 1 year or more.

Multifunctional Monomers

In one aspect, the invention provides a multifunctional monomer having the formula:

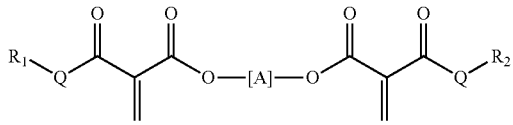

wherein:
each instance of R$^1$ and R$^2$ are independently C$_1$-C$_{15}$ alkyl, C$_2$-C$_{15}$ alkenyl, halo-(C$_1$-C$_{15}$ alkyl), C$_3$-C$_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

-[A]- represents —$(CR^AR^B)_n$—, —$(CR^AR^B)_n$—O(C=O)—$(CH_2)_{1-15}$—(C=O)O—$(CR^AR^B)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

each instance of $R^A$ or $R^B$ is independently H, $C_1$-$C_{15}$ alkyl, $C_2$-$C_{15}$ alkenyl, a moiety represented by the formula:

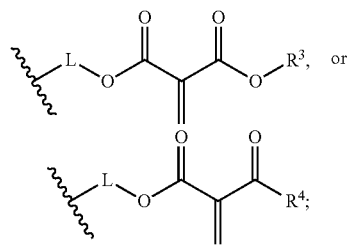

wherein:
- -L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- $R^3$ is independently selected from the group defined in $R^2$ above; and
- $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- —[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group
- each instance of n is independently an integer from 1 to 25; and
- each instance of Q represents —O— or a direct bond.

In another aspect, the invention provides a multifunctional monomer having the formula:

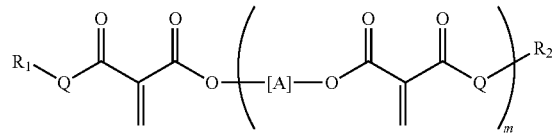

wherein:
each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

-[A]- represents —$(CR^AR^B)_n$—, —$(CR^AR^B)_n$—O(C=O)—$(CH_2)_{1-15}$—(C=O)O—$(CR^AR^B)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

each instance of $R^A$ or $R^B$ is independently H, $C_1$-$C_{15}$ alkyl, $C_2$-$C_{15}$ alkenyl, a moiety represented by the formula:

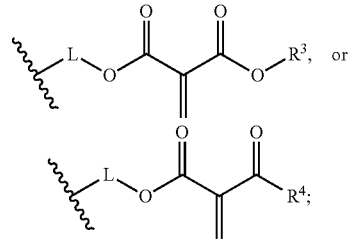

wherein:
- -L- is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- $R^3$ is independently selected from the group defined in $R^2$ above; and
- $R^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl), cycloalkyl, halo cycloalkyl, heterocyclyl, heterocyclyl-(alkyl), aryl, aryl-(alkyl), heteroaryl, $C_1$-$C_{15}$ alkoxy, $C_1$-$C_{15}$ alkylthio, hydroxyl, nitro, azido, cyano, acyloxy, carboxy, ester, each of which may be optionally branched;
- —[CY]— represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group n is an integer from 1 to 25;
m is an integer from 1 to 25;
each instance of Q represents —O— or a direct bond.

In certain embodiments, the invention provides multifunctional monomer having the formula:

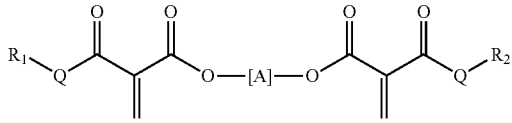

wherein:
each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

[A] represents —$(CH_2)_n$—, —$(CH_2)_n$—O(C=O)—$(CH_2)_{1-15}$—(C=O)O—$(CH_2)_n$—, —$(CH_2)_n$—[CY]—$(CH_2)_n$, a polybutadienyl linking group, a polyethylene glycol linking group, a polyether linking group, a polyurethane linking group, an epoxy linking group, a polyacrylic linking group, or a polycarbonate linking group;

[CY] represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group;

each instance of n is independently an integer from 1 to 25; and
each instance of Q represents —O— or a direct bond.

In other embodiments, the invention provides a multifunctional monomer having the formula:

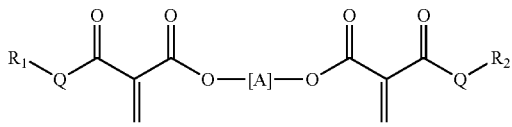

wherein:
each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

[A] represents a linking group derived from $C_1$-$C_{12}$ alkyl diol, any isomer of cyclohexane dimethanol, polybutyl THF, or trimethylolpropane;
each instance of Q represents —O— or a direct bond.

In still other embodiments, the invention provides a multifunctional monomer having the formula:

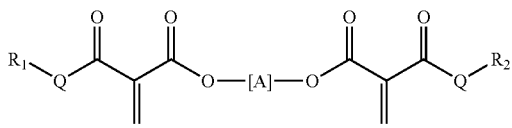

wherein:
each instance of $R^1$ and $R^2$ are independently $C_1$-$C_6$ alkyl or aryl;
-[A]- represents $C_1$-$C_{15}$ alkyl, or $C_3$-$C_6$ cycloalkyl; and
each instance of Q represents —O— or a direct bond.

Synthetic Methods

The present invention provides two routes to the synthesis of multifunctional methylene malonate (MMM) monomers. In specific embodiments, the methods, inter alia, (a) significantly reduces or eliminates the formation of alternative products, (b) significantly reduces or eliminates unwanted consumption of MMM monomers and (c) significantly reduces or eliminates the degradation of MMM monomers in the reaction and subsequent recovery and storage stages. Also disclosed is a route to synthesize multifunctional methylene beta-ketoester (MBK) monomers. Collectively the MMM and MBK are referred to as "multifunctional monomers."

Overall, the chemistry disclosed herein for synthesizing the multifunctional monomers solves the problem of providing multiple highly reactive double bonds into a molecule for subsequent reaction. Specifically, the incorporation of more than one methylene malonate or beta-ketoester functionality, optionally also incorporating a specific backbone functionality, for polymerization that leads to crosslinking or side polymerizations can:

1. Improve solvent resistance or compatibility;
2. Improve or reduce thermal resistance;
3. Incorporate specific performance characteristics, such as toughness, impact resistance, certain chemical resistances, optical properties, property combinations, and the like;
4. Incorporate less expensive backbone raw materials;
5. Increase and/or accelerate cure speed and property build; and
6. Increase or decrease adhesion.

Thus, products which can be formed are wide ranging, from adhesives, coatings, sealants, inks and binders to optical polymers, engineering polymers, composites, reaction injection molded polymers, and water swellable polymers. Also, the specific products made, include assembled objects, rigid and flexible laminates, printed materials and surfaces, composite articles, water and solvent absorbent plastics and devices, textiles, films, sheet goods, construction materials, and so on.

Additionally, reaction with the incorporated methylene double bonds can facilitate incorporating additional chemical functionality, for example via Michael additions:

1. Reactions to incorporate dyes;
2. Reactions to incorporate medicants;
3. Reactions to incorporate anti-fungal agents or similar;
4. Reactions to incorporate catalysts or other functionalities, such as acid groups; and
5. Reactions to incorporate chelating or flocculating agents.

Thus, imagined products are wide ranging, as above, with the additions of heterogeneous or polymer bound catalysts, medicants, and antifungal agents or the like. Also enabled are predyed textile fibers, composites, plastics and reactive formulations, as well as compostable and recyclable water swellable polymers.

Any condensation reaction where the initial functional group and/or the post reaction remaining functional groups do not react readily with the disubstituted vinyl functionality may be utilized. Accordingly, acid catalyzed systems and neutral or acidic functional groups are preferred. Specifically, methylene malonate esters and acids as well as methylene beta-ketoester monomers may be coupled with hydroxyl functional chemicals via direct or trans-esterification.

Heterogeneous catalysts are preferred as they facilitate separation from the typically acidic catalysts that if left in the product could unacceptably inhibit polymerization. Of several catalyst systems tried to date, the enzyme catalyst is showing the best results for making and isolating a polymerizable composition of the multifunctional monomers.

The trans-esterification synthesis route is generally carried out in excess monofunctional methylene malonate (or monofunctional beta-ketoester) without the need for solvent.

Synthesis processes for monofunctional methylene malonates may be found in PCT International Applications filed Oct. 19, 2011, claiming priority to U.S. Provisional Application Ser. Nos. 61/405,029, filed Oct. 20, 2010; 61/405,033, filed Oct. 20, 2010; 61/405,049, filed Oct. 20, 2010; 61/405,056, filed Oct. 20, 2010; 61/405,078, filed Oct. 20, 2010; 61/523,311, filed Aug. 13, 2011; and 61/523,705, filed Aug. 15, 2011, the entire contents each of which are incorporated herein by reference in their entireties.

It is envisioned that methods disclosed herein can be utilized to convert simpler methylene malonate monomers or beta-ketoester monomers into more complex, difficult to produce and/or higher molecular weight monofunctional methylene malonate monomers or methylene beta-ketoester monomers.

A second method for functionalization is illustrated by using the latter described methods and stoichiometry to introduce an additional functionality, such as a hydroxyl group, for derivitization. By example, a diol may be reacted in excess with a methylene malonate or a methylene beta-ketoester to produce a hydroxyl terminated molecule. Specifically, we have reacted an excess of butane diol with diethyl methylene malonate to produce such a molecule. A polymer or resin or larger molecule may then be created by, for example, reacting the new diol with an acid chloride, a lactone, an epoxy, a diacid or an anhydride or similar molecule to produce a higher molecular weight molecule, oligomer or polymer containing methylene malonates in the backbone. Even further, one could add in non-malonate functional acid chlorides, lactones, epoxies, diacids or anhydrides or similar molecules to control the specific amount of incorporated disubstituted vinyl monomer.

Direct Knoevenagel Synthesis

The Knoevenagel reaction with formaldehyde for the synthesis of monofunctional methylene malonate monomers has been previously described. The typical Knoevenagel reaction combines one mole of a malonic acid ester (e.g., a mono- or disubstituted malonate) and one mole of formaldehyde to form, via catalytic (chemical reaction) action in the presence of a basic catalyst and an acidic solvent, a methylene malonate monomer, as depicted in Schematic 1, below.

SCHEME 1: Modified Knoevenagel Reaction

Schematic 1. Knoevenagel reaction with formaldehyde for the synthesis of a methylene malonate.

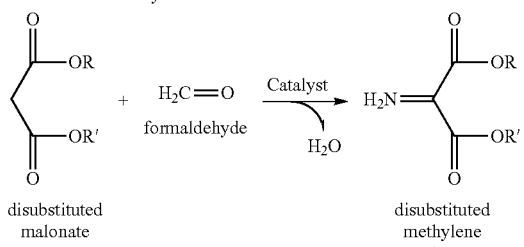

Certain exemplary embodiments contemplate the use of a modified Knoevenagel Synthesis for formation of MMM monomers. As exemplified below, a malonic acid ester or a malonic acid chloride is reacted with a linking group (a diol, a polyol, an aliphatic alcohol comprising two or more hydroxyl groups or a polymeric resin comprising two or more hydroxyl group, a polybutadienyl linking group, or a polyethylene glycol linking group) to form a multifunctional malonic acid ester.

The multifunctional malonic acid ester is then reacted with a source of formaldehyde; optionally in the presence of an acidic or basic catalyst; and optionally in the presence of an acidic or non-acidic solvent, to form a reaction complex from which the MMM monomer can be isolated.

In certain embodiments of the invention, the reacting step is performed at about 60° C. to about 130° C. Depending on the source of formaldehyde used, the reaction step can be performed at about 20° C. to about 50° C., or about 30° C. to about 40° C. In still other instances, particularly, though not limited to, instances when the source of formaldehyde is a gas, the reaction step can be performed at about 0° C. to about 25° C.—provided the reaction mixture is a liquid at such temperatures.

Scheme 1: Formation of MMM through modified Knoevenagel Reaction
SCHEME 2: Transesterification

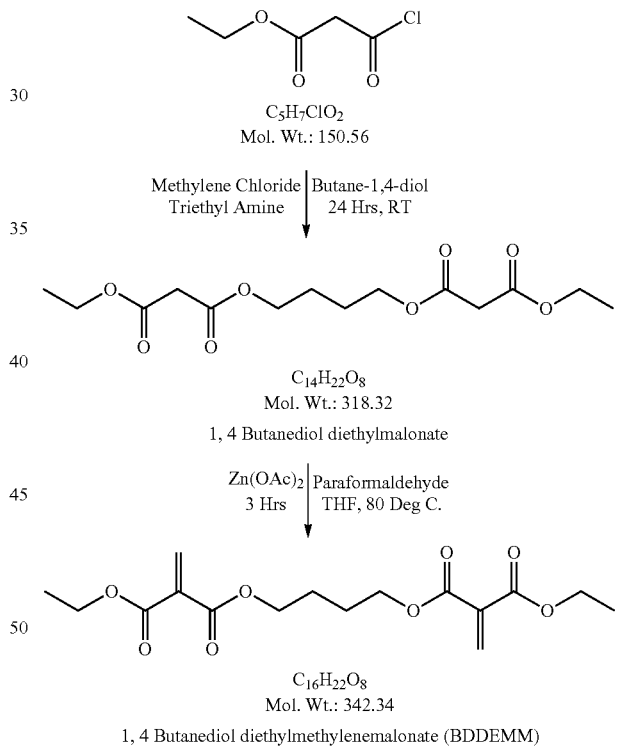

Other exemplary embodiments contemplate the transesterification of monofunctional methylene malonate monomers and monofunctional methylene beta-ketoester monomers for the formation of multifunctional monomers. As illustrated below, a monofunctional methylene malonate monomer is reacted with a diol, polyol, or polymeric resin having two or more hydroxyl groups, to form a multifunctional methylene malonate monomer. A similar reaction scheme may be utilized with a monofunctional methylene beta-ketoester to form a multifunctional methylene beta-ketoester monomer.

SCHEME 2A: Formation of MMM by Transesterification with diol

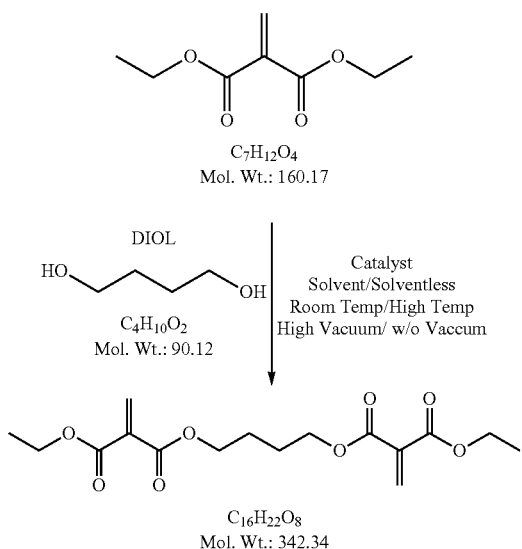

SCHEME 2B: Formation of MMM by Transesterification with polyol

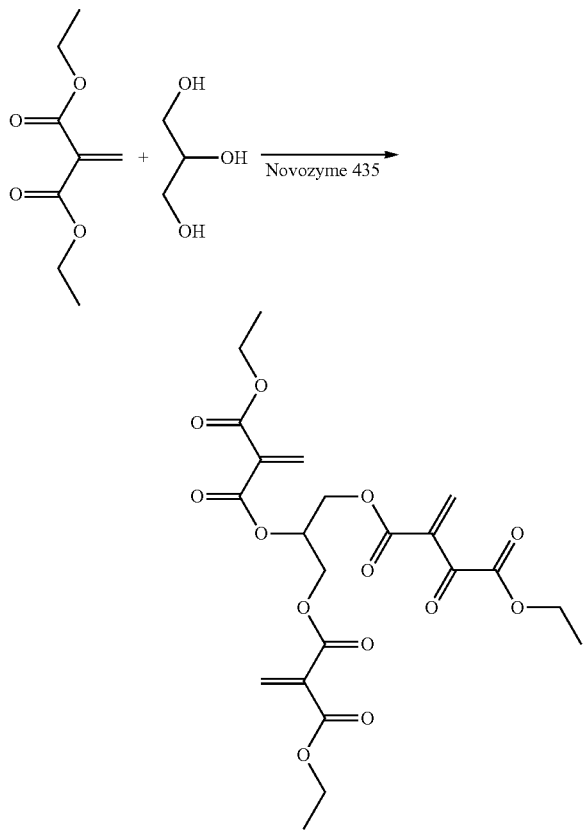

It is envisioned that for the transesterification reaction described above, one could utilize any material having a reactive —OH group including oligomeric and polymeric alcohols, and alcohols which would results in polybutadienyl terminal or linking groups, a polyethylene glycol terminal or linking groups, a polyether terminal or linking groups, a polyurethane terminal or linking groups, an epoxy terminal or linking groups, a polyacrylic terminal or linking groups, or a polycarbonate terminal or linking groups. Such alcohols may be small molecules (linear or branched); polymeric, oligomeric, or resinous. In the instance of terminal groups (as in monofunctional monomers), the alcohol only requires one —OH group. In the instance of linking groups (as in linear or branched multifunctional monomers), the alcohol requires at least two —OH groups It is also envisioned that the multifunctional monomers may be endcapped by transesterification with a methylene beta-ketoester group such as the group defined below

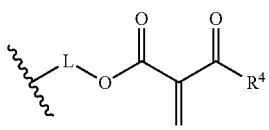

wherein L and $R^4$ are as defined herein.

In still another aspect, the invention provides a method for making a multifunctional methylene malonate monomer. The method comprises:
  (a) reacting a sufficient amount of at least one first methylene malonate monomer with a sufficient amount of a diol, a polyol or a polymeric resin having at least two hydroxyl groups in the presence of a catalyst, under suitable reaction conditions and sufficient time, to form a reaction complex; and
  (b) recovering multifunctional methylene malonate monomer from the reaction complex.

In certain embodiments, the reacting step (a) is performed at room temperature and at atmospheric pressure. In other embodiments, the reacting step (a) is performed at elevated temperature and at atmospheric pressure. In still other embodiments, the reacting step (a) is performed at room temperature and under vacuum. In yet other embodiments, the reacting step (a) is performed at elevated temperature and under vacuum.

In yet another aspect, the invention provides a method of making a multifunctional beta-ketoester monomer comprising:
  (a) reacting a sufficient amount of at least one first methylene beta-ketoester monomer with a sufficient amount of a diol, a polyol or a polymeric resin having at least two hydroxyl groups in the presence of a catalyst, under suitable reaction conditions and sufficient time, to form a reaction complex;
  (b) recovering multifunctional methylene beta-ketoester monomer from the reaction complex.

In still another aspect, the invention provides a method of making a multifunctional methylene malonate monomer comprising:
  (a) reacting a malonic acid ester or a malonic acid chloride with a diol, a polyol, or a polymeric resin comprising at least two hydroxyl groups to form a multifunctional malonic acid ester;
  (b) reacting the multifunctional malonic acid ester formed in step (a) with a source of formaldehyde; optionally in the presence of an acidic or basic catalyst; and optionally in the presence of an acidic or non-acidic solvent; and optionally in the presence of an acid scavenger to form a reaction complex; and
  (c) recovering multifunctional methylene malonate monomer from the reaction complex.

Reactants

In an exemplary embodiment, the Knoevenagel reaction for making multifunctional monomers as disclosed herein includes at least three basic reactants: a malonic acid ester or malonic acid chlorides, a linking group donor (including —OH functional groups) and a source of formaldehyde.

The malonic acid esters or chlorides may be derived or obtained from any source, including any commercial source, derived from nature, other compounds, synthesized by other processes, etc. In certain embodiments, the malonic acid esters are obtained from "green" sources. For example, the malonic acid esters or chlorides can be derived from biological sources, such as via fermentation production systems whereby microorganisms generate the malonic acid esters is direct metabolic by-products of fermentation—or whereby the microorganisms generate metabolic by-products of fermentation that can be then converted inexpensively to the desired malonic acid esters. These fermentation production systems are well-known in the art and may utilize either—or both-microorganisms derived from nature or engineered microorganisms that are specifically designed to produce the desired malonic acid ester products, e.g., recombinant or engineered *Escherichia coli*.

Further reference to the methods, materials and procedures for preparing and/or obtaining monofunctional, difunctional and multifunctional malonic acids and/or malonic acid chlorides can be found in U.S. Pat. No. 7,663,000 (Quinoneimines of malonic acid diamides); U.S. Pat. No. 7,553,989 (Malonic acid monoesters and process for producing the same); U.S. Pat. No. 7,208,621 (Malonic acid monomethyl derivatives and production process thereof); U.S. Pat. No. 7,109,369 (Malonic acid monomethyl derivatives and production process thereof); U.S. Pat. No. 6,794,365 (Malonic acid derivatives, processes for their preparation their use and pharmaceutical compositions containing them); U.S. Pat. No. 6,673,957 (Method for producing alkoxy malonic acid dinitriles); U.S. Pat. No. 6,613,934 (Enantiomerically enriched malonic acid monoesters substituted by a tertiary hydrocarbon radical, and their preparation); U.S. Pat. No. 6,559,264 (Malonic acid ester/triazole mixed blocked HDI trimer/formaldehyde stabilization); U.S. Pat. No. 6,395,931 (Malonic acid and esters thereof); U.S. Pat. No. 6,395,737 (Malonic acid derivatives, processes for their preparation, for their use and pharmaceutical compositions containing them); U.S. Pat. No. 6,284,915 (Process for preparing 2-amino malonic acid derivatives and 2-amino-1,3-propanediol derivatives, and intermediates for preparing the same); U.S. Pat. No. 6,238,896 (Process for producing malonic acid derivatives); U.S. Pat. No. 5,886,219 (Process for preparing malonic acid and alkylmalonic acids); U.S. Pat. No. 5,817,870 (Process for the production of malonic acid or a salt thereof); U.S. Pat. No. 5,817,742 (Polymer-conjugated malonic acid derivatives and their use as medicaments and diagnostic agents); U.S. Pat. No. 5,693,621 (Malonic acid derivatives having antiadhesive properties); U.S. Pat. No. 5,426,203 (Platinum complexes of malonic acid derivatives and process for the preparation thereof); U.S. Pat. No. 5,334,747 (Method of preparing substituted malonic ester anilides and malonic acid monoanilides); U.S. Pat. No. 5,292,937 (Use of malonic acid derivative compounds for retarding plant growth); U.S. Pat. No. 5,210,222 (Process for the production of malonic acid anhydride); U.S. Pat. No. 5,162,545 (Malonic acid dyes and polycondensation products thereof); U.S. Pat. No. 5,039,720 (Aqueous electrophoretic enamel coating materials, which can be deposited at the cathode crosslinked with methane tricarboxylic acid amides of malonic acid derivatives); U.S. Pat. No. 5,021,486 (Hindered amine-substituted malonic acid derivatives of s-triazine); U.S. Pat. No. 4,914,226 (Malonic acid derivatives and methods for their synthesis); U.S. Pat. No. 4,835,153 (Malonic acid derivatives); U.S. Pat. No. 4,736,056 (Process for the production of malonic acid derivative compounds); U.S. Pat. No. 4,698,333 (Use of substituted malonic acid derivatives as agents for combating pests); U.S. Pat. No. 4,578,503 (Alkylated or alkenylated malonic acid or its derivatives having a fluorine); U.S. Pat. No. 4,556,649 (Substituted malonic acid diamide insecticides, compositions and use); U.S. Pat. No. 4,539,423 (Process for preparing diesters of malonic acid); U.S. Pat. No. 4,517,105 (Metalworking lubricant composition containing a novel substituted malonic acid diester); U.S. Pat. No. 4,504,658 (Epimerization of malonic acid esters); U.S. Pat. No. 4,444,928 (Polymeric malonic acid derivatives); U.S. Pat. No. 4,443,624 (Method of preparing malonic acid dialkyl esters); U.S. Pat. No. 4,399,300 (Method of preparing malonic acid dialkyl esters); U.S. Pat. No. 4,329,479 (Process for producing 1,3-dithiol-2-ylidene malonic acid dialkyl esters); U.S. Pat. No. 4,256,908 (Process for preparing diesters of malonic acid); U.S. Pat. No. 4,237,297 (Piperidine containing malonic acid derivatives); U.S. Pat. No. 4,198,334 (Substituted malonic acid derivatives and their use as stabilizers); U.S. Pat. No. 4,154,914 (Process for producing acrylic rubber by copolymerizing acrylic ester and malonic acid derivative having active methylene group); U.S. Pat. No. 4,105,688 (Process for the production of malonic acid dinitrile and purification thereof); U.S. Pat. No. 4,102,809 (Malonic acid composition for thermoparticulating coating); U.S. Pat. No. 4,079,058 (Process of performing cyclization reactions using benzyl or pyridylamino malonic acid derivatives); U.S. Pat. No. 4,046,943 (Malonic acid derivative composition for forming thermoparticulating coating); U.S. Pat. No. 4,036,985 (Mono substituted malonic acid diamides and process of preparing them); U.S. Pat. No. 3,995,489 (Malonic acid derivative composition for forming thermoparticulating coating); U.S. Pat. No. 3,936,486 (Process for the production of malonic acid dinitrile), each of which are incorporated by reference in their entireties by reference herein.

The methods of the invention also contemplate any suitable source of formaldehyde. For example, the formaldehyde may be synthesized, derived from another chemical species (e.g., paraformaldehyde), or obtained from nature or from some other suitable source. In certain embodiments, the formaldehyde is introduced in the form of a gas. In certain embodiments, the formaldehyde is obtained from paraformaldehyde. Commercial sources of formaldehyde and paraformaldehyde are readily available, which may include, for example, trioxane and formalin (e.g., aqueous formaldehyde). In other exemplary embodiments, formaldehyde may be released in another reaction or process and made available for the processes disclosed herein.

The transesterification reaction for making multifunctional methylene malonates of the invention includes at least two basic reactants: a monofunctional methylene malonate monomer or monofunctional methylene beta-ketoester monomer and a linking group donor (including —OH functional groups).

The methods of the invention contemplate any suitable source of monofunctional methylene malonate monomer. Further reference to the methods, materials and procedures for preparing and/or obtaining monofunctional methylene malonate monomers can be found in U.S. Patent Documents: U.S. Pat. Nos. 2,313,501; 2,330,033; 3,221,745; 3,523,097; 3,557,185; 3,758,550; 3,975,422; 4,049,698;

4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and Patent Publications 2004/0076601; WO/2012/054616A2; WO2012/054633A2.

In particular embodiments, the monofunctional methylene malonate monomer can be prepared according to the methods of the PCT International Applications filed Oct. 19, 2011, claiming priority to U.S. Provisional Application Ser. No. 61/405,029, filed Oct. 20, 2010, 61/405,033, filed Oct. 20, 2010, 61/405,049, filed Oct. 20, 2010, 61/405,056, filed Oct. 20, 2010, 61/405,078, filed Oct. 20, 2010, 61/523,311, filed Aug. 13, 2011, and 61/523,705, filed Aug. 15, 2011, the entire contents each of which are incorporated herein by reference in their entireties.

The methods of the invention also contemplate any suitable source of terminal or linking group donors. Such donors include any material having a reactive —OH group including oligomeric and polymeric alcohols, and alcohols which would results in polybutadienyl terminal or linking groups, a polyethylene glycol terminal or linking groups, a polyether terminal or linking groups, a polyurethane terminal or linking groups, an epoxy terminal or linking groups, a polyacrylic terminal or linking groups, or a polycarbonate terminal or linking groups. Such alcohols may be small molecules (linear or branched), polymeric, oligomeric, or resinous. In the instance of terminal groups (as in monofunctional monomers), the alcohol only requires one —OH group. In the instance of linking groups (as in linear or branched multifunctional monomers), the alcohol requires at least two —OH groups In certain embodiments, the source of the linking group may be straight or branched alcohols having two or more hydroxyl groups, polymeric resins comprising two or more hydroxyl groups, represented by [A]-(OH)$_n$ wherein:

[A] represents —(CR$^A$R$^B$)$_n$—, —(CR$^A$R$^B$)$_n$—O (C=O)—(CH$_2$)$_{1-15}$—(C=O)O—(CR$^A$R$^B$)$_n$—, —(CH$_2$)$_n$—[CY]—(CH$_2$)$_n$, a polybutadienyl linking group, a polyethylene glycol linking group, a polyether linking group, a polyurethane linking group, an epoxy linking group, a polyacrylic linking group, or a polycarbonate linking group;

each instance of R$^A$ or R$^B$ is independently H, C$_1$-C$_{15}$ alkyl, C$_2$-C$_{15}$ alkenyl, a moiety represented by the formula:

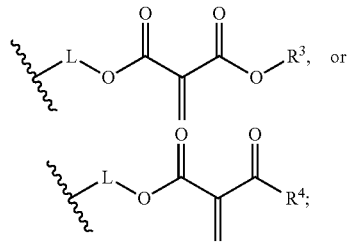

wherein:
L is a linking group selected from the group consisting of alkylene, alkenylene, haloalkylene, cycloalkylene, cycloalkylene, heterocyclylene, heterocyclyl alkylene, aryl-alkylene, heteroarylene or heteroaryl-(alkylene), or alkoxy-(alkylene), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, C$_1$-C$_{15}$ alkoxy, C$_1$-C$_{15}$ alkylthio, hydroxyl, nitro, azido, cyano, acyloxy, carboxy, ester, each of which may be optionally branched;

R$^3$ is independently selected from C$_1$-C$_{15}$ alkyl, C$_2$-C$_{15}$ alkenyl, halo-(C$_1$-C$_{15}$ alkyl), C$_3$-C$_6$ cycloalkyl, halo-(C$_3$-C$_6$ cycloalkyl), heterocyclyl, heterocyclyl-(C$_1$-C$_{15}$ alkyl), aryl, aryl-(C1-C15 alkyl), heteroaryl or heteroaryl-(C$_1$-C$_{15}$ alkyl), or alkoxy —(C1-15 alkyl), each of which may be optionally substituted by C$_1$-C$_{15}$ alkyl, halo-(C$_1$-C$_{15}$ alkyl), C$_3$-C$_6$ cycloalkyl, halo-(C$_3$-C$_6$ cycloalkyl), heterocyclyl, heterocyclyl-(C$_1$-C$_{15}$ alkyl), aryl, aryl —(C$_1$-C$_{15}$ alkyl), heteroaryl, C$_1$-C$_{15}$ alkoxy, C$_1$-C$_{15}$ alkylthio, hydroxyl, nitro, azido, cyano, acyloxy, carboxy, or ester; and R$^4$ is alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl), each of which may be optionally branched and each of which may be optionally substituted by alkyl, haloalkyl, cycloalkyl, halo cycloalkyl, heterocyclyl, heterocyclyl-(alkyl), aryl, aryl-(alkyl), heteroaryl, C$_1$-C$_{15}$ alkoxy, C$_1$-C$_{15}$ alkylthio, hydroxyl, nitro, azido, cyano, acyloxy, carboxy, ester, each of which may be optionally branched;

[CY] represents an alkyl, alkenyl, haloalkyl, cycloalkyl, halo cycloalkyl, heterocyclyl, heterocyclyl alkyl), aryl-(alkyl), heteroaryl or heteroaryl-(alkyl), or alkoxy-(alkyl) group;

each instance of n is independently an integer from 1 to 25; and each instance of Q represents —O— or a direct bond.

By way of illustration only, and not by means of limitation, in certain embodiments the linking group source is a diol, such as ethylene diol, 1,3-propylene diol, 1,2 propylene diol, 1-4-butanediol, 1,2-butane diol, 1,3-butane diol, 2,3-butane diol, or 1,5-pentane diol. In other embodiments, the linking group is a triol, such as 1,2,3-propane triol, 1,2,3-butane triol, or 1,2,4-butane triol. Specific experimental examples are provided below.

Catalysts

Certain embodiments contemplate the use of any suitable acidic or basic catalyst. In certain preferred aspects, it has been surprisingly found that no catalyst at all is required to conduct the reaction.

In certain embodiments, catalysts that are typically used for Knoevenagel reactions with formaldehyde to make monofunctional methylene malonate monomers are contemplated. Such catalysts include, for example, basic catalyst salts, such as, potassium acetate and the neutral co-catalyst copper acetate.

Certain other embodiments contemplate catalysts that heretofore were previously unused in the context of the Knoevenagel reaction with formaldehyde to synthesize monofunctional monomers. Such catalysts include various acidic, basic, neutral, or even amphoteric catalysts.

Acidic catalysts can include, for example, lithium chloride, boron trifluoride etherate, ferric sulfate, zirconium oxychloride, cupric chloride, titanium tetrachloride, zinc chloride, aluminum oxide, or zinc oxide. Accordingly, the acidic catalysts of the invention may include, but are not limited to, paratoluene sulfonic acid, dodecylbenzene sulfonic acid, borontrifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, and zinc chloride. In certain embodiments, the acidic catalyst may include, but is not limited to, Para Toluene Sulfonic Acid (PTSA), Dodecyl Benzene Sulfonic Acid (DBSA), Amberlyst 15, BF3, Zinc Perchlorate, Zirconium Oxide-Sulfated, or Titanium Oxide-Sulfated.

Neutral catalysts can also include silica and other insoluble surface-active agents.

In certain other embodiments, the methods disclosed herein utilize a basic catalyst. Basic catalysts of the invention may include, but are not limited to, potassium acetate, sodium acetate, zinc acetate, zinc acetate dihydrate, aluminum acetate, calcium acetate, magnesium acetate, magnesium oxide, copper acetate, lithium acetate, aluminum oxide, and zinc oxide.

In still further embodiments, the amphoteric catalysts can include, but are not limited to, aluminum oxide, aluminum acetate, zinc acetate, magnesium acetate, and zinc oxide.

In still other embodiments, particularly the transesterification schemes, an enzymatic catalyst is utilized. Such enzymatic catalysts include, but are not limited to Novozym 435.

In still other embodiments, the inventive methods utilize a polymeric catalyst. Such polymeric catalysts include, but are not limited to Dowex 2, Dowex 4, Dowex 5, and Nafion.

In still other embodiments, the present inventors have surprisingly and unexpectedly found that no catalyst is required to conduct the synthesis reaction of the invention. Specifically, in this embodiment, the reaction can be conducted with all of the reactants added to the reaction vessel at the start of the reaction prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Recovery

Embodiments disclosed herein contemplate any suitable method for recovery or isolation of the multifunctional monomer products from the reaction complex. In certain embodiments of the present invention, the recovery method includes filtering an enzymatic catalyst, and use of distillation techniques. In certain other embodiments, the recovery or isolation method involves one or more rounds of a rapid distillation of a condensed vapor phase method, e.g., flash distillation or superheat distillation. In still other embodiments, the recovery or isolation method involves liquid chromatographic separation of multifunctional monomer products. In yet other embodiments, the recovery method involves gas chromatographic separation of vaporized multifunctional methylene malonate products directly from the vapor phase.

Those having ordinary skill in the art will appreciate that simple distillation methods are well known. Simple distillation is a widely used method for separating the components of a liquid mixture, e.g., reaction mixture of the present invention, and depends upon the differences in the ease of vaporization of the components. Typically, the most volatile components of the liquid mixture will vaporize at the lowest temperature, whereas the least volatile components will vaporize at higher temperatures. The vaporized components pass through a cooled tube or condenser causing the components to condense back into their liquid states and deposited in a collector or equivalent vessel. By separating the distillated into sequentially collected fractions ranging from most volatile to least volatile components, the components can be separated. The process can be repeated on any given fraction(s) to further separate the components.

In certain exemplary embodiments disclosed herein, the reaction includes excess monofunctional monomer reactant that must be separated from the multifunctional monomer product. Typically, however, the desired multifunctional monomer product is less volatile than the starting reactant. Thus, it is envisioned that use of distillation as a separation technique would result in the monomer reactant being driven off first, with the product remaining behind, thus requiring further separation techniques.

Those having skill in the art may employ any separation techniques as required to isolate and/or recover the desired multifunctional monomer product. Further, separation and recovery techniques may be used in combination where suitable as known by those having skill in the art.

Compositions

The multifunctional monomers disclosed herein can be incorporated into any number of compositions and products. Certain exemplary formulated compositions may be utilized as adhesives, sealants, coating compositions, inks, paints, and the like. Additionally, polymerizable compositions contemplated herein may be utilized to form polymer-based products such as coatings (e.g., thermal barrier coatings), paint, textile fibers, water-treatment polymers, ink carriers, paint carriers, packaging film, moldings, medical polymers, a polymer film, a polymer fiber, a polymer sheet, and so on. It is envisioned that polymerizable compositions contemplated herein may be utilized as matrix material for composites (wood, fiber, carbon, polymeric) and even be utilized in the filler material.

Embodiments disclosed herein may be formulated to include one or more materials to extend the shelf-life of polymerizable compositions as well as control the onset of cure of the materials. In certain embodiments, the compositions are formulated such that the composition is stable for at least 1 month, or for at least 2 months, or for at least 3 months, or for at least 4 months, or for at least 5 months, or for at least 5-10 months, or for at least 10-20 months, or for at least 20-30 months. Preferably, adhesive compositions comprising the multifunctional monomers of the invention, or other commercial compositions or products, are stable for at least one year.

Such formulation materials include acidic stabilizer, volatile acid stabilizers, acidic gases, free radical stabilizers, sequestering agents, cure accelerators and rheology modifiers.

The present invention contemplates any suitable acidic stabilizer known in the art, including, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymerizable compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Volatile acid stabilizers include any material which can be added to the monomer or polymerizable compositions to extend shelf-life and stabilize the vapor phase above the composition upon storage, e.g., acidic gases. Such volatile acid stabilizers may have a boiling point, for example, less than about 200° C.; less than about 170° C.; or less than about 130° C.

Acidic gases include any gaseous material which can be added to the monomer or polymerizable compositions to extend shelf-life and stabilize the vapor phase above the composition upon storage. Such acid gases can include, but are not limited to, $SO_2$ or $BF_3$.

For each of these acidic stabilizing materials, such acidic stabilizer can be present in a concentration of about 0.1 ppm to about 100 ppm; about 0.1 ppm to about 25 ppm; or about 0.1 ppm to about 15 ppm.

Free radical stabilizers can include any material capable of stabilizing or inhibiting free radical polymerization of the material upon standing. In one embodiment, the free radical stabilizers are phenolic free radical stabilizers such as, HQ (hydroquinone), MEHQ (methyl-hydroquinone), BHT (butylated hydroxytoluene) and BHA (butylated hydroxyanisole). In certain embodiments, the free radical stabilizers are present in a concentration of 0.1 ppm to 10,000 ppm; 0.1 ppm to 3000 ppm; or 0.1 ppm to 1500 ppm. In certain other embodiments, particularly where a free radical or ultraviolet cure will be utilized on the materials of the invention, the free radical stabilizers are present in a concentration of 0.1 ppm to 1000 ppm; 0.1 ppm to 300 ppm; or 0.1 ppm to 150 ppm.

Sequestering agents include any material capable of enhancing the bonding of materials containing acid salts such as paper or wood. Such sequestering agents include, but are not limited to crown ethers, silyl crowns, calixarenes and polyethylene glycols. Sequestering agents also enhance the utility of surface accelerators that are acid salts applied to surfaces to control the rate of cure of the materials.

Cure accelerators include any material capable of speeding the rate of cure of the multifunctional monomers of the invention. Cure accelerators also include any material capable of speeding the cure through volume of the multifunctional monomers of the invention. Such cure accelerators include but are not limited to sodium or potassium acetate; acrylic, maleic or other acid salts of sodium, potassium lithium copper and colbalt; salts such as tetrabutyl ammonium fluoride, chloride, or hydroxide; or chemically basic materials such as amines and amides, or salts of polymer bond acids, or of benzoate salts, 2,4-pentanedionate salts, sorbate salts, or propionate salts. Such cure accelerators can be added directly to the compositions of the invention or applied to the material to be bonded prior to addition of the composition of the invention.

Rheology modifiers include any material which can modify the viscosity of the compositions of the invention as well as thixotropic properties for greater utility in certain applications. Rheology modifiers include, but are not limited to, hydroxyethylcellulose, ethyl hydroxyethylcellulose, methylcellulose, polymeric thickeners, pyrogenic silica or a combination thereof.

In certain embodiments, the compositions may include tougheners. Such tougheners include, but are not limited to, acrylic rubbers; polyester urethanes; ethylene-vinyl acetates; fluorinated rubbers; isoprene-acrylonitrile polymers; chlorosulfonated polyethylenes; homopolymers of polyvinyl acetate; and reaction products of the combination of ethylene, methyl acrylate and monomers having carboxylic acid cure sites, which once formed are then substantially free of processing aids and anti-oxidants; and combinations thereof. In certain embodiments, the tougheners include those disclosed in U.S. Pat. No. 4,440,910 (O'Connor), directed to rubber toughened cyanoacrylate compositions through the use of certain organic polymers as toughening additives that are elastomeric, i.e., rubbery, in nature, such as acrylic rubbers; polyester urethanes; ethylene-vinyl acetates; fluorinated rubbers; isoprene-acrylonitrile polymers; chlorosulfonated polyethylenes; and homopolymers of polyvinyl acetate. In certain embodiments, the toughener is an elastomeric polymer which is a copolymer of methyl acrylate and ethylene, manufactured by DuPont, under the name of VAMAC, such as VAMAC N123 and VAMAC B-124. VAMAC N123 and VAMAC B-124 are reported by DuPont to be a master batch of ethylene/acrylic elastomer. In other embodiments, the toughener may be the DuPont materials called VAMAC B-124, N123, VAMAC G, VAMAC VMX 1012 or VCD 6200. In other instances, the toughener may be a rubber toughening component having (a) reaction products of the combination of ethylene, methyl acrylate and monomers having carboxylic acid cure sites, (b) dipolymers of ethylene and methyl acrylate, and combinations of (a) and (b), which once the reaction products and/or dipolymers are formed are then substantially free of processing aids, such as the release agents octadecyl amine (reported by DuPont to be available commercially from Akzo Nobel under the tradename ARMEEN 18D), complex organic phosphate esters (reported by DuPont to be available commercially from R.T. Vanderbilt Co., Inc. under the tradename VAN-FRE VAM), stearic acid and/or polyethylene glycol ether wax, and anti-oxidants, such as substituted diphenyl amine (reported by DuPont to be available commercially from Uniroyal Chemical under the tradename NAUGARD 445). Commercial examples of such rubber tougheners include VAMAC VMX 1012 and VCD 6200 rubbers, and these may also be used.

The polymerizable compositions contemplated herein may also optionally include other additives, such as plasticizing agents, thixotropic agents, natural or synthetic rubbers, filler agents, and reinforcing agents, etc. Such additives are well known to those skilled in the art.

The polymerizable compositions of the invention may optionally include at least one plasticizing agent that imparts flexibility to the polymer formed from the multifunctional monomers. The plasticizing agent preferably contains little or no moisture and should not significantly affect the stability or polymerization of the monomer. Such plasticizers are useful in polymerizable compositions to be used in any application in which flexibility of the adhesive or polymer product is desirable.

Examples of suitable plasticizers include, without limitation, acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester gluterates and polyester adipates.

The addition of plasticizing agents in amounts less than about 60 weight %, or less than about 50 weight %, or less than about 30 weight %, or less than about 10 weight %, or less than about 5 weight %, or less than about 1 weight % or less, provides increased film strength (e.g., toughness) of the polymerized material over polymerized materials not having such plasticizing agents.

The polymerizable compositions disclosed herein may also optionally include at least one thixotropic agent, i.e., the property of exhibiting a high fluidity during deformation by force of a sprayer, roller or trowel, but losing the fluidity when left at rest. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513 or 4,510,273, the disclosures of which are hereby incorporated in their entireties.

The polymerizable compositions disclosed herein may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The polymerizable compositions disclosed herein may also optionally comprise one or more other reinforcing agents (e.g., fibrous reinforcements) other than natural or synthetic rubber to impart impact resistance and/or to impart structural strength or to provide shape or form. Examples of such agents are well known in the art. Examples of suitable fibrous reinforcement include PGA microfibrils, collagen microfibrils, cellulosic microfibrils, and olefinic microfibrils. The compositions may also contain colorants such as dyes, pigments, and pigment dyes. Examples of suitable colorants include 6-hydroxy-5-[(4-sulfophenyl)axo]-2-naphthalene-sulfonic acid (FD+C Yellow No. 6); 9-(o-carboxyphenoyl)-6-hydroxy-2,4,5,7-tetraiodo-3H-xanthen-3-one monohydrate (FD+C Red No. 3); and 2-(1,3-dihydro-3-oxo-5-sulfo-2H-indol-2-ylidene)-2,3-dihydro-3-oxo-1H-indole-5-sulfonic acid (FD+C Blue No. 2), wherein the suitable colorant should not destabilize the monomer.

The polymerizable compositions disclosed herein may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the polymerizable compositions disclosed herein, difunctional monomeric cross-linking agents may be added to the monomer compositions of this invention. Such cross-linking agents are known. U.S. Pat. No. 3,940,362 to Overhults, which is hereby incorporated in its entirety by reference, discloses such crosslinking agents.

Other compositions and additives contemplated for use in compositions disclosed herein include additional stabilizers, accelerators, plasticizers, fillers, opacifiers, inhibitors, thixotrophy conferring agents, dyes, fluorescence markers, thermal degradation reducers, adhesion promoters, thermal resistance conferring agents and combinations thereof, and the like, some of which are exemplified by U.S. Pat. Nos. 5,624,669; 5,582,834; 5,575,997; 5,514,371; 5,514,372; 5,312,864 and 5,259,835, the disclosures of all of which are hereby incorporated in their entirety by reference.

Depending on whether the material is a monomer-based composition (e.g., inks, adhesives, coatings, sealants or reactive molding) or a polymer-based composition (e.g., fibers, films, sheets, medical polymers, composite polymers and surfactants), one having ordinary skill in the art will have the knowledge and skill by which to formulate such compositions and/or products without undue experimentation having suitable amounts, levels and combinations of the above types of additives and components.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

The following examples illustrate various exemplary embodiments of the methods described in this disclosure.

Analytical Methods

The structures of monomers of this invention were confirmed using one or more of the following procedures.

NMR

In certain instances, routine one-dimensional NMR spectroscopy was performed on either a 400 MHz Varian® spectrometer or a 400 MHz Bruker® spectrometer. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.

In other certain instances, routine NMR spectroscopy was performed on a 300 MHz Bruker NMR spectrometer. Samples were dissolved in deuterated chloroform and were referenced to the solvent peak at 7.26 ppm. As needed, an internal standard of hexamethyldisiloxane (HMDS) was added for absolute quantitation. 1H NMR was used for certain samples, with 13C NMR, DEPT-135, and two-dimensional HSQC (Heteronuclear Single Quantum Correlation) spectroscopy used as needed to validate structures. HMDS appears at 0.06 ppm in the 1H spectrum and at 1.94 in the 13C spectrum.

GC/MS

In certain embodiments, electron impact mass spectra (EI-MS) were obtained with a Hewlett Packard 5970 mass spectrometer equipped Hewlett Packard 5890 Gas Chromatograph with. The ion source was maintained at 270° C.

For certain other embodiments, structural characterization of the multifunctional monomers, were obtained using two types of mass spectrometry techniques. The first technique used is electrospray ionization (ESI) which is coupled with both ion trap (IT) and Fourier transform ion cyclotron resonance (FT-ICR) mass analyzers. ESI is a soft ionization technique where ions are produced directly from the liquid phase. In this analysis, formic acid was added to a diluted solution of DEMM multifunctional monomer in acetonitrile, thus producing positively charged or protonated molecular ions. These ions are directly measured in the FT-ICR mass analyzer. Mass measurement in the FT-ICR cell is extremely accurate because it is the frequency of the ion cyclotron motion of the excited ions that is measured. Frequency can be measured very accurately and is directly proportional to mass/charge ratio. The ion trap mass analyzer is used here for MSn analysis. In the ion trap, collision induced dissociation is used to fragment the molecular ions so that structural information can be obtained. These fragment ions can also be measured very accurately in the FT-ICR cell.

Electrospray Ionization Mass Spectrometry (ESI/MS)

Electrospray ionization mass spectra were obtained using a Thermo LTQ-FT, a hybrid instrument consisting of a linear ion trap mass analyzer and a Fourier transform ion cyclotron resonance (FT-ICR) mass analyzer. MS/MS spectra were obtained in the ion trap by collision with helium at a normalized collision energy of 25. Accurate mass measurements were obtained from the FT-ICR scans.

Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

atm atmosphere
br s broad singlet
C Celsius
d doublet
dd doublet of doublets
MM methylene malonate
HQ hydroquinone
GC-MS Gas Chromatograph mass spectroscopy
g gram
h hour, hours
1H NMR proton nuclear magnetic resonance
J coupling constant (NMR spectroscopy)
L liter
M mol L-1 (molar)
m multiplet
MHz megahertz
min minute, minutes
mL milliliter
mM micromolar
mol mole
MS mass spectrum, mass spectrometry
m/z mass-to-charge ratio
N equivalents L-1 (normal)
NMR Nuclear Magnetic Resonance
pH negative logarithm of hydrogen ion concentration
q quartet
rt room temperature
s singlet
t triplet General Methodology. Transesterification Reaction Investigations were made to provide multifunctional monomers (e.g., methylene malonates and methylene beta-ketoesters) via a transesterification process. Multifunctional monomers provide opportunities to cross-link, for enhanced physical properties, and to functionalize the molecules for wider applicability.

The general experiment procedure is outlined below:
1) Follow reasonable safety precautions such as working in a functioning fume hood, review and follow safety data sheet recommendations, exercise appropriate caution when working with liquid nitrogen, use personal protective equipment, exercise caution when handling hot glassware.
2) Unless otherwise specified, test and measurement conditions are:
   a. Procedure 1:
      i. ~55° C.
      ii. ~50 torr vacuum
   b. Procedure 2:
      i. ~70° C.
      ii. ~100 torr vacuum
3) Procedure:
   a. Clean and dry an appropriately sized round bottom flask.
   b. Add catalyst (e.g., Novazym 435) to the flask at 20 weight percent of the volume of starting material (e.g., diethyl methylene malonate DEMM); an appropriate amount of starting material (e.g., DEMM), and an appropriate amount of OH-containing linking group (e.g., diol, polyol, polymeric resin, etc). For a diol, the starting material is added at 5× molar ratio of diol to ensure adequate stoichiometric amounts plus desired excess.
   c. Provide appropriate stir mechanisms, vacuum set up and collection apparatuses.
   d. Heat the reaction vessel, under vacuum, and under gentle agitation. Vacuum is utilized to pull off alcohol generated as a side product.
   e. Collect reaction samples at appropriate time intervals to monitor progress of the reaction (e.g., 4 hours, 6 hours, 8 hours). Stabilize the reaction complex with a suitable stabilizer. (Samples were initially analyzed with H-NMR and TLC to show product formation.)
   f. Transfer reaction complex to a non-reactive bottle (e.g., HDPE) while filtering the catalyst.
   g. Employ suitable separation techniques to isolate and remove reaction product (e.g., multifunctional monomer) from excess starting material (e.g., DEMM).
4) Results and Analysis:

Unless otherwise specified, the diethyl methylene malonate (DEMM) starting material in the reactions discussed below contained a small amount of diethyl malonate (DEM) as an impurity. Both DEM and DEMM are able to participate in the transesterification reaction. The malonate $CH_2$ appears at 3.3 ppm in the 1H NMR and at 41 ppm in the 13C NMR spectra. The carbonyl for the malonate appears at 166 ppm. These peaks can be seen in all spectra of these mixtures.

DEMM:

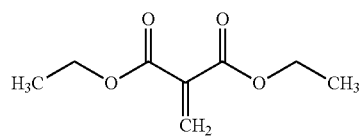

DEM:

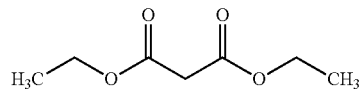

For NMR analysis, samples were diluted in deuterated chloroform prior to $^1$H NMR spectroscopy at 300 MHz (Bruker). A more concentrated sample was also prepared in a solution of 0.01 M Cr(acac)$_3$ in deuterated chloroform and was analyzed by quantitative $^{13}$C NMR spectroscopy at 75 MHz.

Example 1: Reaction of DEMM and 1,6-Hexanediol (HD) by Transesterification

The reaction scheme disclosed herein was performed using DEMM and 1,6-hexanediol. The following monomer was obtained.

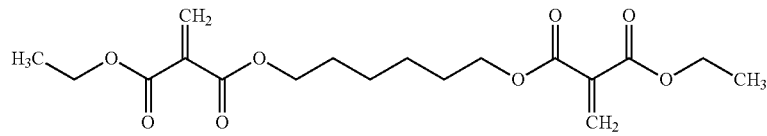 [SMILES: C=C(C(=O)OCC)C(=O)OCCCCCCOC(=O)C(=C)C(=O)OCC]

NMR: The $^1$H NMR spectrum is shown in FIG. 1, of U.S. Pat. No. 9,512,058, incorporated herein by reference. Peak assignments are annotated. Free 1,6-hexanediol shows a peak at 3.6 ppm. The NMR spectrum shows essentially complete consumption of the hexanediol. The broad feature at 2.5 ppm is due to some loss of the double bond during the reaction. The $^{13}$C NMR spectrum (bottom) and the DEPT-135 spectrum (top) are shown in FIG. 2, of U.S. Pat. No. 9,512,058, incorporated herein by reference. Free 1,6-hexane diol would have a peak at 63 ppm. The ester is clearly shown at 65 ppm. The NMR spectra support the proposed structure, although extended structures cannot be ruled out (i.e., higher order oligomers).

ESI/MS: A 1:20000 dilution of the DEMM-1,6-hexanediol multifunctional in acetonitrile with 1% formic acid was directly infused into the electrospray source. The masses of the protonated ions and their corresponding relative intensities for the DEMM-1,6-hexanediol multifunctional synthesis product are shown in FIGS. 14 and 15, of U.S. Pat. No. 9,512,058, incorporated herein by reference. FIGS. 14 and 15 are the same sample but differ in the mass range scanned. The major ions present and the elemental formulas of these ions are listed in Table 1.

TABLE 1

Ions detected in the ESI/MS analysis of DEMM-1,6-hexanediol multifunctional and the corresponding elemental formula and mass measurement error.

| Accurate Mass Measurement (m/z) | Error (ppm) | Elemental Formula |
| --- | --- | --- |
| 173.08088 | 0.256 | $[C_8H_{12}O_4 + H]^+$ |
| 195.06284 | 0.306 | $[C_8H_{12}O_4 + Na]^+$ |
| 359.17014 | 0.267 | $[C_{17}H_{26}O_8 + H]^+$ |
| 371.17015 | 0.285 | $[C_{18}H_{26}O_8 + H]^+$ |
| 393.15209 | 0.230 | $[C_{18}H_{26}O_8 + Na]^+$ |
| 417.21203 | 0.290 | $[C_{20}H_{32}O_9 + H]^+$ |
| 439.19395 | 0.195 | $[C_{20}H_{32}O_9 + Na]^+$ |
| 545.25934 | 0.160 | $[C_{26}H_{40}O_{12} + H]^+$ |
| 557.25940 | 0.264 | $[C_{27}H_{40}O_{12} + H]^+$ |
| 569.25942 | 0.293 | $[C_{28}H_{40}O_{12} + H]^+$ |
| 591.24139 | 0.307 | $[C_{28}H_{40}O_{12} + Na]^+$ |
| 615.30129 | 0.280 | $[C_{30}H_{46}O_{13} + H]^+$ |
| 755.34862 | 0.208 | $[C_{37}H_{54}O_{16} + H]^+$ |
| 767.34870 | 0.309 | $[C_{38}H_{54}O_{16} + H]^+$ |
| 813.39055 | 0.237 | $[C_{40}H_{60}O_{17} + H]^+$ |

The ions detected are the ions formed from the addition of a hydrogen from the acid or from the addition of sodium from the surrounding solvent or environment. The ion at m/z 173 represents the protonated unreacted DEMM which is expected to be present because DEMM was used in excess during the synthesis of the DEMM-1,6-hexanediol product. The sodium adduct of the DEMM is the ion present at m/z 195. The ion at m/z 371 is the most abundant ion present and corresponds to the protonated molecular ion of the DEMM-1,6-hexanediol product with the structure shown below. The sodium adduct for this molecule is also present at m/z 393. Present as a minor ion at m/z 359, is the multifunctional without the methylene group.

Another minor species present at m/z 417 is the result of the addition of one ethanol across the methylene double bond as shown below. The sodium adduct of the molecule is also detected at m/z 439.

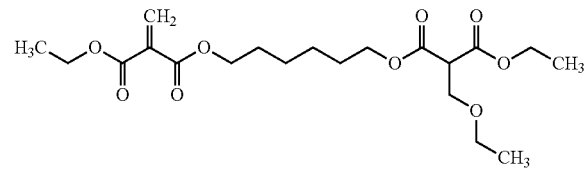 [SMILES: C=C(C(=O)OCC)C(=O)OCCCCCCOC(=O)C(COCC)C(=O)OCC]

The molecular ion at m/z 569 represents the higher order DEMM-1,6-hexanediol multifunctional product represented below and is the second most abundant ion in FIG. 14. The sodium adduct of this higher order multifunctional is also present at m/z 591. Other ions present at m/z 545 and m/z 557 can be attributed to the presence of the multifunctional present missing two and one methylene groups, respectively.

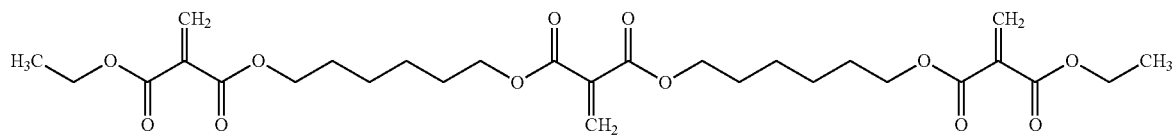 [SMILES: C=C(C(=O)OCC)C(=O)OCCCCCCOC(=O)C(=C)C(=O)OCCCCCCOC(=O)C(=C)C(=O)OCC]

The protonated molecular ion for an even higher order multifunctional is found at m/z 767. The minor ion at m/z 755 can be attributed to the lack of one methylene group within this higher order structure.

Example 2: Reaction of DEMM and Cyclohexanedimethanol (CHDM) by Transesterification The reaction scheme disclosed herein was performed using DEMM and cyclohexanedimethanol. The following monomer was obtained.

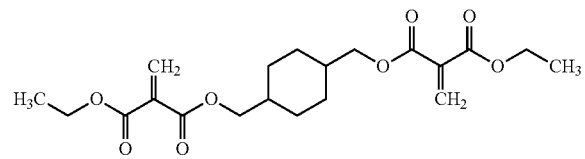 [SMILES: C=C(C(=O)OCC)C(=O)OCC1CCC(COC(=O)C(=C)C(=O)OCC)CC1]

NMR: The cyclohexanedimethanol used was a mixture of cis and trans, which means that the NMR spectrum of the starting material shows two sets of peaks. FIG. 3, of U.S. Pat. No. 9,512,058, incorporated herein by reference is the $^1$H NMR spectrum of the reaction product. Unreacted starting material would show up very close to the malonate impurity at 3.3-3.4 ppm. However, it is clear that most of the alcohol has reacted. The $^{13}$C and DEPT-135 spectra are shown in FIG. 4, of U.S. Pat. No. 9,512,058, incorporated herein by reference and for comparison, an overlay of the reaction product and an Aldrich library spectrum of the cyclohexanedimethanol starting material are shown in FIG. 5, of U.S. Pat. No. 9,512,058, incorporated herein by reference. The shift of the starting material is consistent with the product shown above. Again, NMR would not be able to easily rule out the presence of higher order oligomers.

Example 3: Reaction of DEMM and Poly-Tetrahydrofuran (Poly-THF) by Transesterification The reaction scheme disclosed herein was performed using DEMM and poly-tetrahydrofuran. The following monomer was obtained.

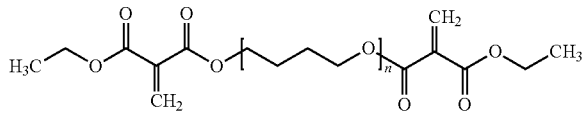

NMR: The poly(THF) starting material used has an average molecular weight of 250, which corresponds to an average repeat unit of n=3. The $^1$H NMR spectrum is shown in FIG. 6, of U.S. Pat. No. 9,512,058, incorporated herein by reference. Unreacted alcohol groups would appear at 3.6 ppm, but this is also where the ether peaks will show up, making it difficult to discern the structure from this spectrum.

The $^{13}$C NMR and DEPT-135 spectra are shown in FIG. 7, of U.S. Pat. No. 9,512,058, incorporated herein by reference. The peak at 65 ppm is due to the ester. Unreacted alcohol would appear at 62 ppm, very close to the ethyl ester peak. However, a quantitative $^{13}$C NMR experiment shows very little extra area of the 62 ppm peak vs. the 14 ppm peak of the ethyl, indicating very little unreacted alcohol present, supporting the structure shown above.

Example 4: Reaction of DEMM and 1,8-octanediol by Transesterification

The reaction scheme disclosed herein was performed using DEMM and 1,8-octanediol. The following monomer was obtained.

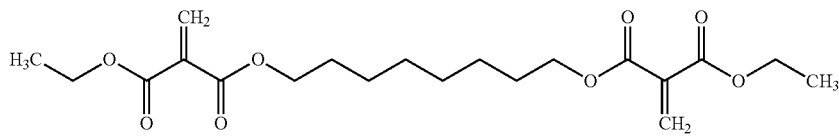 [SMILES: C=C(C(=O)OCC)C(=O)OCCCCCCCCOC(=O)C(=C)C(=O)OCC]

The 1H NMR spectrum (FIG. 8), of U.S. Pat. No. 9,512,058, incorporated herein by reference, and the 13C NMR and DEPT-135 spectra (FIG. 9), of U.S. Pat. No. 9,512,058, incorporated herein by reference, show evidence of complete transesterification of the diol with the DEMM. The double bond (peaks at 6.4 ppm in the 1H and at 134 and 135 ppm in the 13C spectra) is also intact.

Example 5: Reaction of DEMM and 1,10-decanediol by Transesterification

The reaction scheme disclosed herein was performed using DEMM and 1,8-octanediol. The following monomer was obtained.

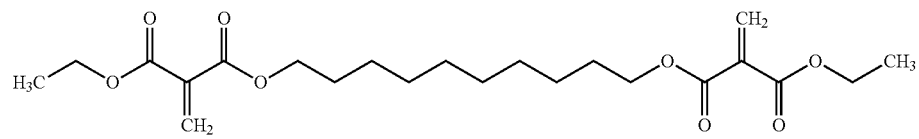 [SMILES: C=C(C(=O)OCC)C(=O)OCCCCCCCCCCOC(=O)C(=C)C(=O)OCC]

The 1H NMR spectrum (FIG. 10), of U.S. Pat. No. 9,512,058, incorporated herein by reference, and the 13C NMR and DEPT-135 spectra (FIG. 11), of U.S. Pat. No. 9,512,058, incorporated herein by reference, show evidence of complete transesterification of the diol with the DEMM. The double bond (peaks at 6.4 ppm in the 1H and at 134 and 135 ppm in the 13C spectra) is also intact.

Example 6: Reaction of DEMM and Trimethylolpropane by Transesterification

The reaction scheme disclosed herein was performed using DEMM and trimethylolpropane. The following monomer was obtained.

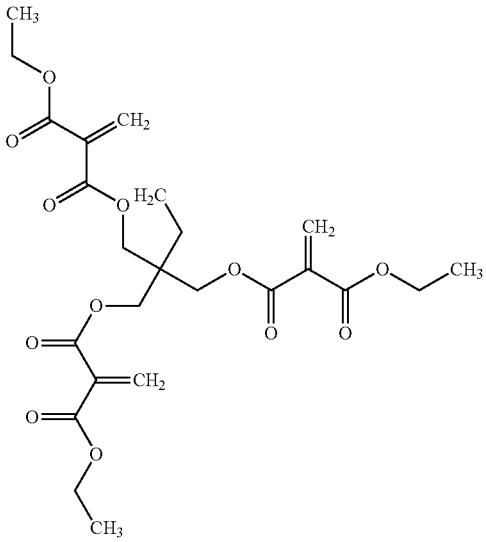 [SMILES: C=C(C(=O)OCC)C(=O)OCC(CC)(COC(=O)C(=C)C(=O)OCC)COC(=O)C(=C)C(=O)OCC]

The $^1$H NMR spectrum is shown in FIG. 12, of U.S. Pat. No. 9,512,058, incorporated herein by reference. This spectrum is more complicated. While there is some intact double bond left at 6.4 ppm, the peaks in the 2.4-2.8 ppm range are likely due to polymerization of the double bond. The $^{13}$C and DEPT-135 NMR spectra are shown in FIG. 13, of U.S. Pat. No. 9,512,058, incorporated herein by reference. The peak at 133.5 ppm ($CH_2$) and the peak at 135 ppm (quaternary) support the geminal double bond. The peak at 68 ppm is the esterified TMP and the peak at 66 ppm is due to the unreacted TMP alcohols. Other peaks present are likely due to side reactions (Michael Addition by the alcohols).

Example 7. Reaction of DEMM and 1,3-benzene dimethanol by Transesterification

The reaction scheme disclosed herein is performed using appropriate reactant to obtain the following monomers:

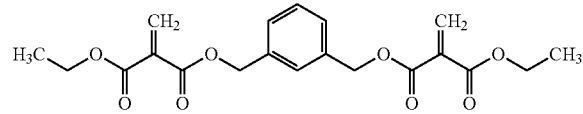 [SMILES: C=C(C(=O)OCC)C(=O)OCc1cccc(COC(=O)C(=C)C(=O)OCC)c1]

The $^1$H NMR spectra are shown in FIGS. 16 and 17, of U.S. Pat. No. 9,512,058, incorporated herein by reference. The peaks in the 5.0-5.3 ppm region are consistent with the transesterification. There is some double bond left intact at 6.5 ppm. However, the peaks between 2.4 and 2.9 ppm are likely caused by polymerization of the double bond. The 4-hour reaction (FIG. 16) shows more intact double bond than the 8-hour reaction (FIG. 17).

Example 8. Reaction of DEMM and Poly(Butadiene) Hydroxyl Terminated by Transesterification The reaction scheme disclosed herein can be performed using poly(butadiene) hydroxyl terminated as a starting material:

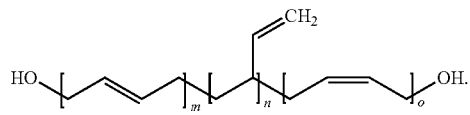

One exemplary product formed by the transesterification of DEMM with poly(butadiene) hydroxyl terminated may be represented as:

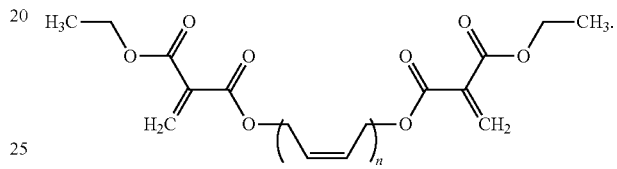

Example 9. Additional Examples

The reaction schemes disclosed herein may also be performed using the following starting materials: a polyester or oligomer/polymer containing one or more ester groups in a linear or cyclic structure, including, but not limited to, polybutyl succinate, polyethylene adipate, polycaprolactone (made from cyclic caprolactone). In such instances, functionality which would interfere with the transesterification catalysts of cause instability in the final product containing methylene malonate functionality should be avoided.

The resulting methylene malonate functionality can be terminal or within the overall molecular structure. Such materials can be copolymers with for example styrene, acrylonitrile, ethers, and ketones that contain sufficient ester functionality to allow ester interchange.

EQUIVALENTS

Those skilled in the art will recognize, or be able to ascertain using no more than routine experimentation, many equivalents to the specific embodiments of the invention described herein. Such equivalents are intended to be encompassed by this invention.

What is claimed is:
1. A multifunctional monomer having the formula:

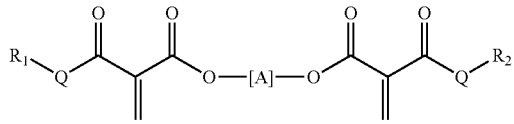

wherein:
each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), aryl, aryl-(C1-C15 alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), aryl, aryl—($C_1$-$C_{15}$ alkyl), $C_1$-$C_{15}$ alkoxy, $C_1$-$C_{15}$ alkylthio, hydroxyl, nitro, azido, cyano, acyloxy, carboxy, or ester;

[A] is independently selected from a polybutadienyl linking group, a polyurethane linking group, an epoxy linking group, a polyacrylic linking group, a polycarbonate linking group, a polyester linking group, a $C_3$-$C_6$ cycloalkyl linking group, a triol linking group, or a dimethyl benzene linking group;
and
each instance of Q is —O— or a direct bond.

2. A multifunctional monomer according to claim 1, wherein [A] is independently selected a polybutadienyl linking group, a polyurethane linking group, an epoxy linking group, a polyacrylic linking group, polycarbonate linking group, $C_3$-$C_6$ cycloalkyl linking group or a triol linking group.

3. A multifunctional monomer according to claim 1, wherein:
[A] is independently selected from a linking group derived from any isomer of cyclohexane dimethanol or trimethylol propane.

4. A multifunctional monomer according to claim 1, wherein
each instance of $R^1$ and $R^2$ are independently $C_1$-$C_6$ alkyl or $C_3$-$C_6$ cycloalkyl; and
-[A]- is independently selected from a $C_3$-$C_6$ cycloalkyl.

5. The multifunctional monomer according to claim 1, wherein each instance Q is —O—.

6. The multifunctional monomer according to claim 1, wherein each instance Q is a direct bond.

7. A multifunctional monomer according to claim 1, having the formula:

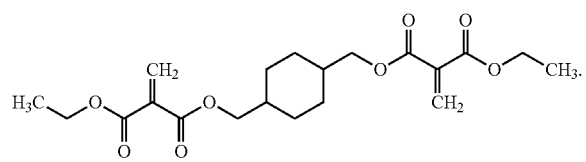 [SMILES: C=C(C(=O)OCC)C(=O)OCC1CCC(COC(=O)C(=C)C(=O)OCC)CC1]

8. A multifunctional monomer according to claim 1, having the formula:

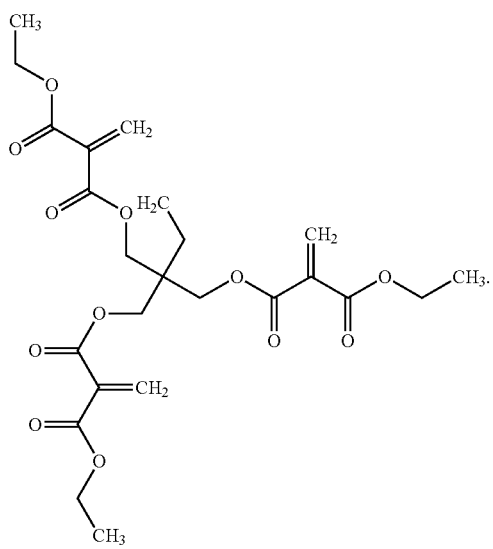 [SMILES: C=C(C(=O)OCC)C(=O)OCC(CC)(COC(=O)C(=C)C(=O)OCC)COC(=O)C(=C)C(=O)OCC]

9. A multifunctional monomer according to claim 1, having the formula:

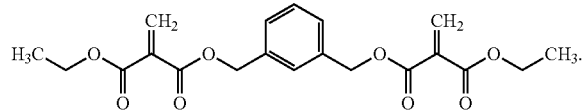 [SMILES: C=C(C(=O)OCC)C(=O)OCc1cccc(COC(=O)C(=C)C(=O)OCC)c1]

10. A multifunctional monomer according to claim 1, wherein A is independently selected from a polyester linking group and the polyester linking group is selected from copolymers containing styrene, acrylonitrile, ethers, and ketones that contain ester functionality to allow ester interchange.

11. A multifunctional monomer according to claim 1, wherein $R^1$ and $R^2$ are selected from $C_{1-6}$ alkyl or a $C_3$-$C_6$ cycloalkyl.

12. A multifunctional monomer having the formula:

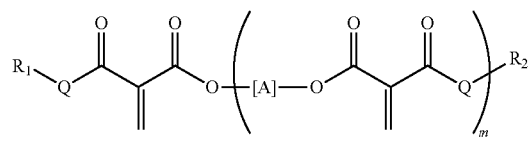

wherein:
each instance of $R^1$ and $R^2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), aryl, aryl-($C_1$-$C_{15}$ alkyl), or alkoxy —($C_1$-$C_{15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), aryl, aryl—($C_1$-$C_{15}$ alkyl), $C_1$-$C_{15}$ alkoxy, $C_1$-$C_{15}$ alkylthio, hydroxyl, nitro, azido, cyano, acyloxy, carboxy, or ester;

-[A]- is independently selected from a polybutadienyl linking group, a polyurethane linking group, an epoxy linking group, a polyacrylic linking group, or a polycarbonate linking group, a polyester linking group, polytetrahydrofuran, a $C_3$-$C_6$ cycloalkyl linking group, a triol linking group, or a dimethyl benzene linking group;

m is an integer from 1 to 25; and
each instance of Q is independently selected from —O— or a direct bond.

13. A multifunctional monomer according to claim 12, wherein A is independently selected from a polybutadienyl linking group, a polyurethane linking group, an epoxy linking group, a polyacrylic linking group, a polycarbonate linking group, a polytetrahydrofuran linking group, $C_3$-$C_6$ cycloalkyl linking group, or a triol linking group.

14. A multifunctional monomer according to claim 12, wherein A is independently selected from any isomer of cyclohexane dimethanol, polybutyl tetrahydrofuran, or trimethylol propane.

15. A multifunctional monomer according to claim 12, wherein A is independently selected from a polybutadienyl linking group, a polyurethane linking group, an epoxy linking group, a polyacrylic linking group, a polycarbonate linking group.

16. A multifunctional monomer according to claim 12 wherein A is independently selected from a $C_3$-$C_6$ cycloalkyl linking groups.

17. A multifunctional monomer according to claim 12, wherein A is independently selected from a polyester linking group and the polyester linking group is selected from copolymers containing styrene, acrylonitrile, ethers, and ketones that contain ester functionality to allow ester interchange.

18. The multifunctional monomer according to claim 12, wherein each instance Q is —O—.

19. The multifunctional monomer according to claim 12, wherein each instance Q is a direct bond.

20. A multifunctional monomer according to claim 12, wherein $R^1$ and $R^2$ are selected from $C_{1-6}$ alkyl or a $C_3$-$C_6$ cycloalkyl.

* * * * *